United States Patent [19]
Waeber et al.

[11] Patent Number: 5,880,261
[45] Date of Patent: Mar. 9, 1999

[54] TRANSCRIPTION FACTOR ISLET-BRAIN 1 (IB1)

[76] Inventors: Gerard Waeber, Chemin de la reuyre 59, 1008 Jouxtens; Christophe Bonny, Rue du Lyon 7, Geneva, both of Switzerland

[21] Appl. No.: 859,201

[22] Filed: May 20, 1997

[30] Foreign Application Priority Data

Apr. 3, 1997 [GB] United Kingdom ............... 9706731
  May 15, 1997 [GB] United Kingdom ............... 9709920

[51] Int. Cl.⁶ ............................................. C07K 14/47
[52] U.S. Cl. ......................................................... 530/350
[58] Field of Search ............................... 530/350; 514/12

[56] References Cited

PUBLICATIONS

Ngo et al, The Protein Folding Problem and Tertiary Structure Prediction, Mertz et al (eds), Birkhauser, Boston, pp. 492–495, 1994.
Gibbs et al, cell, vol. 79, pp. 193–198, Oct. 21, 1994.
Martin et al, J. of Biological Chem., vol. 270 (15), pp. 8822–8828, Apr. 14, 1995.
Jackman et al, J. of Biological Chem., vol. 270 (13) pp. 7029–7032, Mar. 31, 1995.
Yin et al, J. of Biological Chem., vol. 270 (17), pp. 10147–10160, Apr. 28, 1995.
Orci, Reduced b–cell glucose transporter in new onset diabetic BB rats, Nov. 1990, J. Clin Invest 86, 1615–22.
Thorens, The loss of GLUT2 expression by glucose–unresponsive b cells of db/db mice is reversible and is induced by the diabetic environment, Jul. 1992, J Clin Invest 90, 77–85.
Waeber, Transcriptional activation if the GLUT2 gene by the IPF–1/STFD–1/IDX–1 homeobox factor, Mol Endocrin 10, 1327–34.
Waeber,A 338–bp proximal fragment of the glucose transporter type 2 (GLUT2) promoter drives reporter gene expression in the pancreatic islets of trangenic mice, 1995, Mol & Cell Endocrin, 114, 205–15.
Bonny, Pancreatic–specific expression of the glucose transporter type 2 gene: identification of cis–elements and islet–specific trans–acting factors, 1995, Mol Endocrin 9, 1413–26.

Thorens, Cloning and functional expression in bacteria of a novel glucose transporter present in liver, intestine, kidney and b–pancreatic islet cells, 1988, Cell 55, 281–90.
Leloup, Glucose transporter 2 (GLUT2): expression in specific brain nuclei, 1994, Brain Res. 638, 221–26.
Waeber, Characterization of the murine high Km Glucose transporter GLUT2 gene and its transcriptional regulation by glucose in a differentiated insulin–secreting cell line, 1994, J Biol Chem 269, 26912–19.
Rencurel, Requirement of glucose metabolism for regulation of glucose transporter type 2 (GLUT2) gene expression in liver, 1996, Biochem J 314, 903–909.
Ohneda, GLUT2 expression and function in b–cells of GK rats with NIDDM, 1993, Diabetes 42, 1065–72.
Orci, Localization of the pancreatic beta cell glucose transporter to specific plasma membrane domain, 1989, Science, 245, 295–97.
Johnson, Underexpression of b cell high Km glucose transporters in noninsulin–dependent diabetes, 1990, Science 250, 546–549.
Rencurel, cAMP prevents the glucose–mediated stimulaltion of GLUT2 gene transcription in hepatocytes, 1997, Boichem J 322, 441–48.
Unger diabetic hyperglycemia: link to impaired glucose transport in pancreatic b cells, 1991, Science 251, 1200–1205.
Orci, Evidence that down–regulation of b–cell glucose transporters in non–insulin–dependent diabetes may be the cause of diabetic hyperglycemia, 1990, Proc Natl Acad Sci 87, 9953–57.
Thorens, Reduced expression of the liver/beta–cell glucose transporter isoform in glucose–insensitive pancreatic beta cells of diabetic rats, 1990, Proc natl Acad Sci 87, 6492–96.

*Primary Examiner*—Terry McKelvey
*Attorney, Agent, or Firm*—Luann Cserr

[57] ABSTRACT

Transcriptional activator Islet-Brain 1 (IB1) is disclosed which is involved in the control of the GLUT2 and insulin genes by interacting with homologous cis-regulatory elements of the GLUT2 and insulin promoters, and to materials and methods deriving from this work. In particular, the use of IB1 nucleic acid, IB1 polypeptides and anti-IB1 antibodies in the diagnosis, and prophylactic and therapeutic treatment of conditions such as diabetes and neurological diseases such as dementia and/or parkinsonism is disclosed.

4 Claims, 16 Drawing Sheets

Fig. 1A

|       |                                                              |                          |
|-------|--------------------------------------------------------------|--------------------------|
| IB1   | RTGARGUFPAYYAIEVTKEPEHMAALAKNS............KGNDVLCAAMQKIATTR  |                          |
| E47   | R-ERRMANNARERLRVRDINEAFRELGRMC............KIILQQAVQVIIGLE    |                          |
| MyoD  | A-DRRKAATMRERRRLSKVNEAFETLKRCT............K-VETLRNAIRYIEGLQ  |                          |
| c-myc | N-VKRRTHNVLERQRRNELKRSFFALRDQI............K-VLKKATAYILSVQ    |                          |
| E12   | K-ERRVANNARERLRVRDINEAFKELGRMC............K-LIHQAVSVIENL     |                          |
| ITF-1 | R-ERRMANNARERVRVRDINEAFRELGRMC............K-LILQQAVQVIIGLE   |                          |

*Fig. 1B* hIB1

```
   1  AACCCTCACT AAAGGGAACA AAACGCTGGA GCTCGCVCGC CTGCAGGTCG
  51  ACACTACGTG GATCCAAAGA ATTCcGGCAC GAGTGCCTGC CTCTCCGAGG
 101  ACTCCACGCC TGATGAACCC GACGTCCATT TCTCCAAGAA ATTCCTGAAC
 151  GTCTTCATGA GTGGCCGCTC CCGCTCCTCC AGTGCTGAGT CCTTCGGGCT
 201  GTTCTCCTGC ATCATCAACG GGGAGGAGCA GGAGCAGACC CACCGGGCCA
 251  TATTCAGGTT TGTGCCTCGA CACGAAGACG AACTTSAGCT GGAAGTGGAT
 301  GACCCTCTGC TAGTGGAGCT CCAGGCTGAA GACTACTGGT ACGAGGCCTA
 351  CAACATGCGC ACTGGTGCCC GGGGTGTCTT TCCTGCCTAT TACGCCATCG
 401  AGGTCACCAA GGAGCCCGAG CACATGGCAG CCCTGGCCAA AAACAGTGAC
 451  TGGGTGGACC AGTTCCGGGT GAAGTTCCTG GGCTCAGTCC AGGTTCCCTA
 501  TCACAAGGGC AATGACGTCC TCTGTGCTGC TATGCAAAAG ATTGCCACCA
 551  CCCGCCGGCT CACCGTGCAC TTTAACCCGC CCTCCAGCNG TGTCCTGGAG
 601  ATCAGCGTGC GGGGTGTGAA GATAGGCGTC AAGGCCGATG ACTCCCAGGA
 651  GGCCAAGGGG AATAAATGTA GCCACTTTTT CCAGTTAAAA AACATCTCTT
 701  TCTGCGGATA TCATCCAAAG AACAACAAGT ACTTTGGGTT CATCACCAAG
 751  CACCCCGCCG ACCACCGGTT TGCCTGCCAC GTCTTTGTGT CTGAAGACTC
 801  CACCAAAGCC CTGGCAGAGT CCGTGGGGAG AGCATTCCAG CAGTTCTACA
 851  AGCAGTTTGT GGAGTACACC TGCCCCACAG AAGATATCTA CCTGGAGTAG
 901  CTGTGCAGCC CGCCTCTGCG TCCCCAGCCT CAGGCCAGTG CCAGGACAGC
 951  TGGCTGCTGA CAGGATGTGG CACTGCTTTA GGAGGGGACT GCCACCGCCA
1001  GGAGGACAAG GAAGT
```

*Fig. 1C* hIB1 x rIb1

```
  1 ..............................CLSEDS   6
                                  ||||||
401 PCFGDYSDESDSATVYDNCASASSPYESAIGEEYEEAPQPRPPTCLSEDS 450

7 TPDEPDVHFSKKFLNVFMSGRSRSSSAESFGLFSCIINGEEQEQTHRAIF  56
    |||||||||||||||||||||||||||||||||||:|||||:|||||||
451 TPDEPDVHFSKKFLNVFMSGRSRSSSAESFGLFSCVINGEEHEQTHRAIF 500

57 RFVPRHEDELXLEVDDPLLVELQAEDYWYEAYNMRTGARGVFPAYYAIEV 106
    ||||||||| |||||||||||||||||||||||||||||||||||||||
501 RFVPRHEDELELEVDDPLLVELQAEDYWYEAYNMRTGARGVFPAYYAIEV 550

107 TKEPEHMAALAKNSDWVDQFRVKFLGSVQVPYHKGNDVLCAAMQKIATTR 156
    |||||||||||||||:|||||||||||||||||||||||||||||||||
551 TKEPEHMAALAKNSDWIDQFRVKFLGSVQVPYHKGNDVLCAAMQKIATTR 600

157 RLTVHFNPPSSXVLEISVRGVKIGVKADDSQEAKGNKCSHFFQLKNISFC 206
    |||||||||| |||||||||||||||||:.|||||||||||||||||||
601 RLTVHFNPPSSCVLEISVRGVKIGVKADEAQEAKGNKCSHFFQLKNISFC 650

207 GYHPKNNKYFGFITKHPADHRFACHVFVSEDSTKALAESVGRAFQQFYKQ 256
    |||||||||||||||||||||||||||||||||||||||||||||||||
651 GYHPKNNKYFGFITKHPADHRFACHVFVSEDSTKALAESVGRAFQQFYKQ 700

257 FVEYTCPTEDIYLE*LCSP...PLRPQPQASARTAG.......C*QDVAL 296
    ||||||||||||||.|   ||.|.|  :. ||:         .: :|
701 FVEYTCPTEDIYLE*QQPPSLQPLSPRPVLGQLTADRMLYCHERMGE*GL 750

297 L*EGTATARRTRK.................................... 309
    |  .|.  . |.|
751 LGSGGRGLGRGRCSLL*YMGLD*SMEDSTGSLGAGEGQGWGGGQASGHKG 800
```

*Fig. 1D*

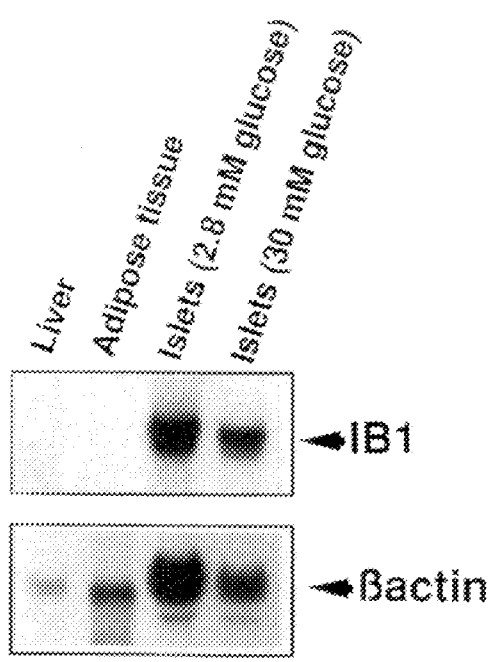 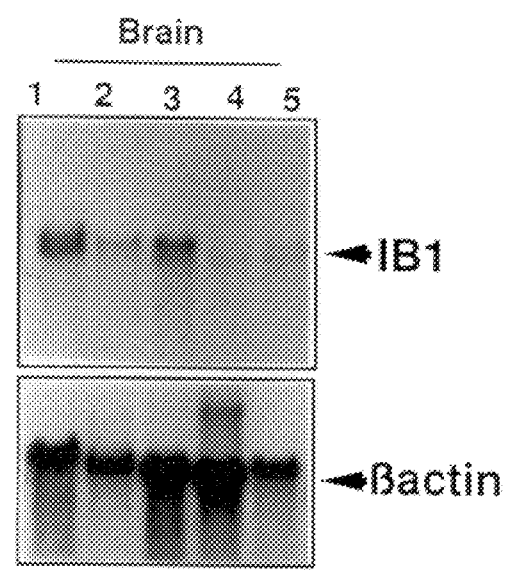
*Fig. 2C*    *Fig. 2D*

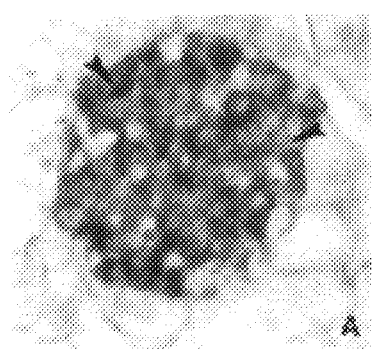
*Fig. 4A*
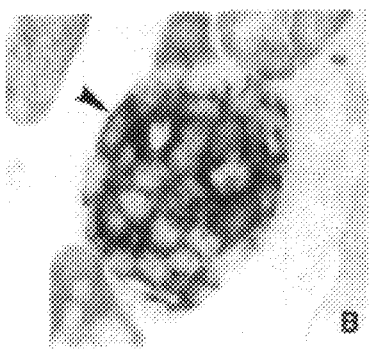
*Fig. 4B*
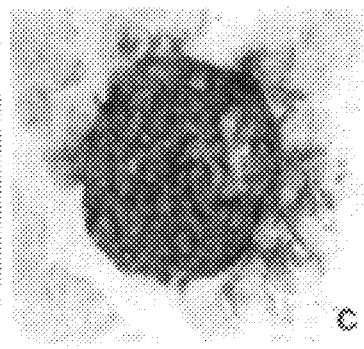
*Fig. 4C*
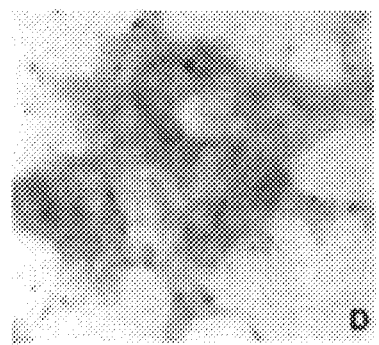
*Fig. 4D*
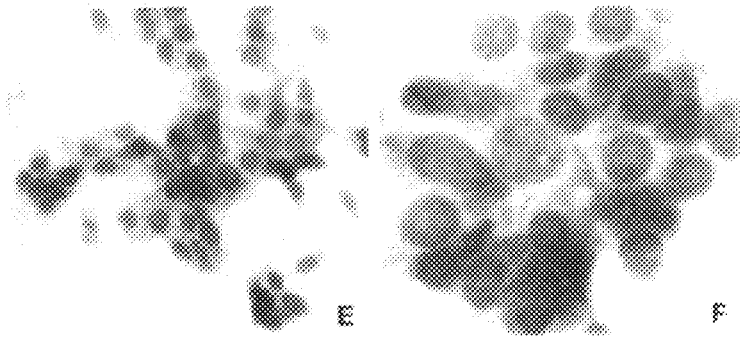
*Fig. 4E*
*Fig. 4F*

TRANSCRIPTION FACTOR ISLET-BRAIN 1 (IB1)

FIELD OF THE INVENTION

The present invention relates to identification and characterisation of Islet-Brain 1 (IB1), a transcriptional activator that is involved in the control of the GLUT2 and insulin genes by interacting with homologous cis-regulatory elements of the GLUT2 and insulin promoters, and to materials and methods deriving from this work. In particular, the present invention relates to the uses of IB1 nucleic acid, IB1 polypeptides and anti-IB1antibodies in the diagnosis, and prophylactic and therapeutic treatment of conditions such as diabetes and neurological diseases such as dementia and/or parkinsonism.

BACKGROUND OF THE INVENTION

The GLUT2 facilitated glucose transporter isoform is a membrane protein present in the pancreatic β-insulin-secreting cells, the basolateral membrane of intestinal and kidney absorptive cells, in hepatocytes and in a subset of neurons (21,31,44). In these cells, GLUT2 catalyzes the transepithelial transport of glucose. In pancreatic islets, GLUT2 allows a rapid equilibration of glucose between the extracellular space and the interior of the cells and it may play a crucial role in the glucose signaling mechanism leading to insulin secretion (43). However, the relative importance of GLUT2 in the sensing of the β-pancreatic cells to glucose remains debated. In human β-cells, the level of expression of GLUT2 is low and the intracellular glucokinase activity seems to be the rate-limiting step in the glycolytic pathway (5,11). On the other hand, insulinoma cells that had lost their normal glucose responsiveness have low GLUT2 content, but some glucose sensitivity may be recovered after reintroducing GLUT2 expression through stable transfection of these cells (10,16). Furthermore, transgenic mice that express GLUT2 antisense RNAs driven by the insulin promoter led to an 80% reduction in GLUT2 which was paralleled by a decreased glucose-induced insulin secretory response and by the onset of diabetes (48). These observations are critical since several experimental models of diabetes have shown that GLUT2 expression is dramatically reduced specifically in the pancreatic β-cells, and that this mechanism could participate to the onset of the disease (18,29,30,32,45–47). Therefore, while GLUT2 levels are unchanged or even upregulated in several tissues such as the liver and the intestine during the hyperglycemic conditions observed in diabetes, the same gene undergoes a drastic dysregulation only in the pancreatic islets.

A fragment of the murine GLUT2 promoter has been cloned and shown to be glucose-responsive when transfected into differentiated insulin-producing cells or into hepatocytes (35,36,52). Important cis-regulatory sequences were identified within this promoter region including a functionally responsive PDX-1 element, a cyclic AMP responsive element, and three cis elements termed GTI, GTII and GTIII (3,36,53). The presence of GTI, II and III are both sufficient and necessary to confer pancreatic-specific expression to a reporter gene in vitro or in vivo, using a transgenic mice approach (3,51). GTI and GTIII have been previously shown to bind distinct, but ubiquitously expressed trans-acting factors.

SUMMARY OF THE INVENTION

The present invention is based on successful expression cloning of a transcription factor that binds to the GTII element of the GLUT2 and insulin genes from a differentiated insulin-secreting cDNA library.

This factor is abundantly expressed in the pancreatic islets and in the brain and has been named IB-1 for Islet-Brain 1. The IB1cDNA encodes a 714 amino acid protein with a proline-rich region and a putative basic helix-loop-helix domain (bHLH). The IB1 gene is highly expressed in the pancreatic islets and in the brain and to a much lesser extent in the heart and the kidney. In the Langerhans islets and in β-cell lines, these transcripts are translated into immunodetectable cytoplasmic and nuclear protein. When tested in vitro, IB1 bound specifically to the GTII cis element of the GLUT2 gene and to an homologous regulatory sequence of the insulin promoter termed RIPE3. This rat insulin promoter element 3 (RIPE3) is an important enhancer sequence sufficient to confer β-cell specific expression to the insulin gene. Functionally, IB1 transactivated the proximal region of the GLUT2 promoter linked to a luciferase reporter gene and was also a potent activator of the insulin gene. This effect is mediated through the RIPE3 sequence as demonstrated by the observation that multiple copies of this enhancer sequence cloned 5' of an heterologous promoter was transactivated by an expression vector encoding IB1 in transient transfection studies. IB1appeared to function only in insulin-secreting cells as no transactivation was observed in non-pancreatic or in glucagon-producing cell lines. These data demonstrate the presence of a novel transcriptional activator abundantly expressed in the endocrine pancreas and which participates to the proper β-cell specific control of the GLUT2 and the insulin genes through homologous sequences present in both promoters.

The nucleic acid and amino acid sequences of rat IB1 are shown in FIG. 1A. The present inventors have also located two human IB1 genes on chromosomes 17 and 11. A portion of the human nucleic acid and amino acids sequences corresponding to amino acid residues 445 to 714 of the rat sequence is set out in FIGS. 1C and 1D.

The human cDNA was constructed as RNA using tissue obtained from a surgically removed human insulinoma. Poly $A^+$ RNA was extracted and a cDNA library constructed and subsequently screened with a radiolabelled rat IB1 cDNA probe. This allowed the inventors to isolate the human cDNA encoding IB1. This cDNA was then used as a probe to clone the human IB1 gene from a bacterial artificial chromosome (BAC). Several clones were obtained and part of them sequenced. The above protocol can be used to complete the sequencing of the human IB1 nucleic acid using techniques well known in the art.

The IB1 gene exists in human as two genes: one intronless gene located in chromosome 17q21–22 and the other, multiexonic, located in chromosome lip. The chromosomal mapping was obtained by FISH experiments and PCR of hybrid cells (hamster-human) using as a probe the intronless or multiexonic IB1 gene. So far no evidence suggests that either of these genes is a pseudogene. Both genes are likely to be transcribed and translated into IB1 products. The chromosomal localization is important as the 17q21 localization of the first IB1 gene is the closest known human marker of a gene responsible for familial dementia and parkinsonism (see Yamaoka et al, Am. J. Hum. Genet., 59:1306–1312, 1996). As several families have been described as carriers of an abnormal gene function within this 17q21 region when they were also carriers of this kind of familial dementia, we can conclude that IB1 would be the gene responsible for this disease. This is reinforced by the observation that IB1is expressed in the brain of rat, mouse and human species and in tissues similar in their ontology (islets of Langerhans).

Accordingly, in a first aspect, the present invention provides an isolated IB1 polypeptide comprising:

(a) a polypeptide having the amino acid sequence set out in FIG. 1A or 1D;

(b) a polypeptide having at least an 80% amino acid sequence homology with the amino acid sequence set out in FIGS. 1A or 1D;

(c) a polypeptide which is a mutant, variant, derivative or allele of a polypeptide of (a) or (b); or, (d) a fragment of a polypeptide of (a), (b) or (c) exhibiting a biological property of full length IB1 protein.

In a further aspect, the present invention provides an isolated nucleic acid molecule encoding an IB1 polypeptide. The rat and human IB1 nucleic acid sequences are set out in FIGS. 1A (SEQ ID NO:1) and 1C (SEQ ID NO:3).

In further aspects, the present invention provides an expression vector comprising the above IB1 nucleic acid operably linked to control sequences to direct its expression, and host cells transformed with the vectors. The present invention also includes a method of producing IB1 proteins comprising culturing the host cells and isolating the IB1protein thus produced.

In a further aspect, the present invention provides an expression vector comprising IB1 nucleic acid for use in methods of gene therapy, e.g. in the treatment of patients unable to produce sufficient IB1 or to engineer cell lines capable of producing IB1.

In a further aspect, the present invention provides a cell line for transplantation into a patient, the cell line being transformed with nucleic acid encoding an IB1 protein, and being capable of producing and secreting functional IB1 proteins. In one embodiment, the cell lines can be encapsulated, e.g. in a biocompatible polymer so that the IB1produced by the cells line can be released into the patient, while preventing rejection by the immune system of the host.

In a further aspect, the present invention provides a pharmaceutical composition comprising one or more IB1 polypeptides as defined above.

In further aspects, the present invention provides the above IB1 polypeptides for use in methods of medical treatment. The present invention further provides the use of the IB1 polypeptides in the preparation of medicament for activating the GLUT2 or insulin promoters leading to the production of GLUT2 or insulin. Preferably, the activation takes place in a cell specific manner, e.g. in β-cells. This could be used in the treatment of conditions treatable using insulin or GLUT2, such as diabetes.

IB1 could also be used as an agent which maintains a state of differentiation within in a cell, i.e. acts as an anti-apoptotic agent. Thus, IB1can be used as an anti-neoplastic agent, e.g. as a drug to control or treat some cancers. As an example, insulinomas are human tumours which undergo dedifferentiation and divide. Thus, IB1 could act as a differentiation agent to treat these cells. A further application of IB1 is in the treatment of brain tumours.

In a further aspect, the present invention provides the use of the IB1 polypeptides in screening candidate compounds for IB1 biological activity, e.g. to find peptidyl or non-peptidyl mimetics of the IB1 proteins to develop as lead compounds in pharmaceutical research.

In a further aspect, the present invention provides antibodies capable of specifically binding to the above IB1 proteins. These antibodies can be used in assays to detect and quantify the presence of IB1 protein, in methods of purifying IB1 proteins, and in pharmaceutical compositions, e.g. to neutralize IB1in conditions in which its overexpression has deleterious effects. As an example, we have found that IB1 was overexpressed in a patient who died from dementia and parkinsonism. Accordingly, reagents such as antibodies which block the expression of IB1 or neutralize IB1 in the tissues in which it is overexpressed can be used for treating such conditions. Polyclonal antibodies to the N-terminal portion (residues 1–280) of the IB1 protein of FIG. 1A is exemplified below.

In a further aspect, the present invention method for determining the presence of IB1 nucleic acid and/or mutations within an IB1 nucleic acid sequence in a test sample comprising detecting the hybridisation of test sample nucleic acid to a nucleic acid probe based on the IB1 nucleic acid sequences set out in FIG. 1A or 1C.

In a further aspect, the present invention provides the use of IB1 nucleic acid as defined above in the design of antisense oligonucleotides to restrict IB1 expression in a population of cells, i.e. phosphorothiolated or chloresterol linked oligonucleotides which can facilitate internalization and stabilization of the oligonucleotides.

In a further aspect, the present invention provides a method of amplifying a nucleic acid test sample comprising priming a nucleic acid polymerase reaction with nucleic acid encoding an IB-1 protein as defined above. The present invention also provides the use of the above nucleic acid in the search for mutations in the IB1 genes, e.g. using techniques such as single stranded conformation polymorphism (SSCP).

By way of example, the present invention will now be described in more detail with reference to the accompanying figures.

BRIEF DESCRIPTION OF THE FIGURES

FIGS. 1A–1D

IB1cDNA and Predicted Protein Sequence.

Figure 1A:
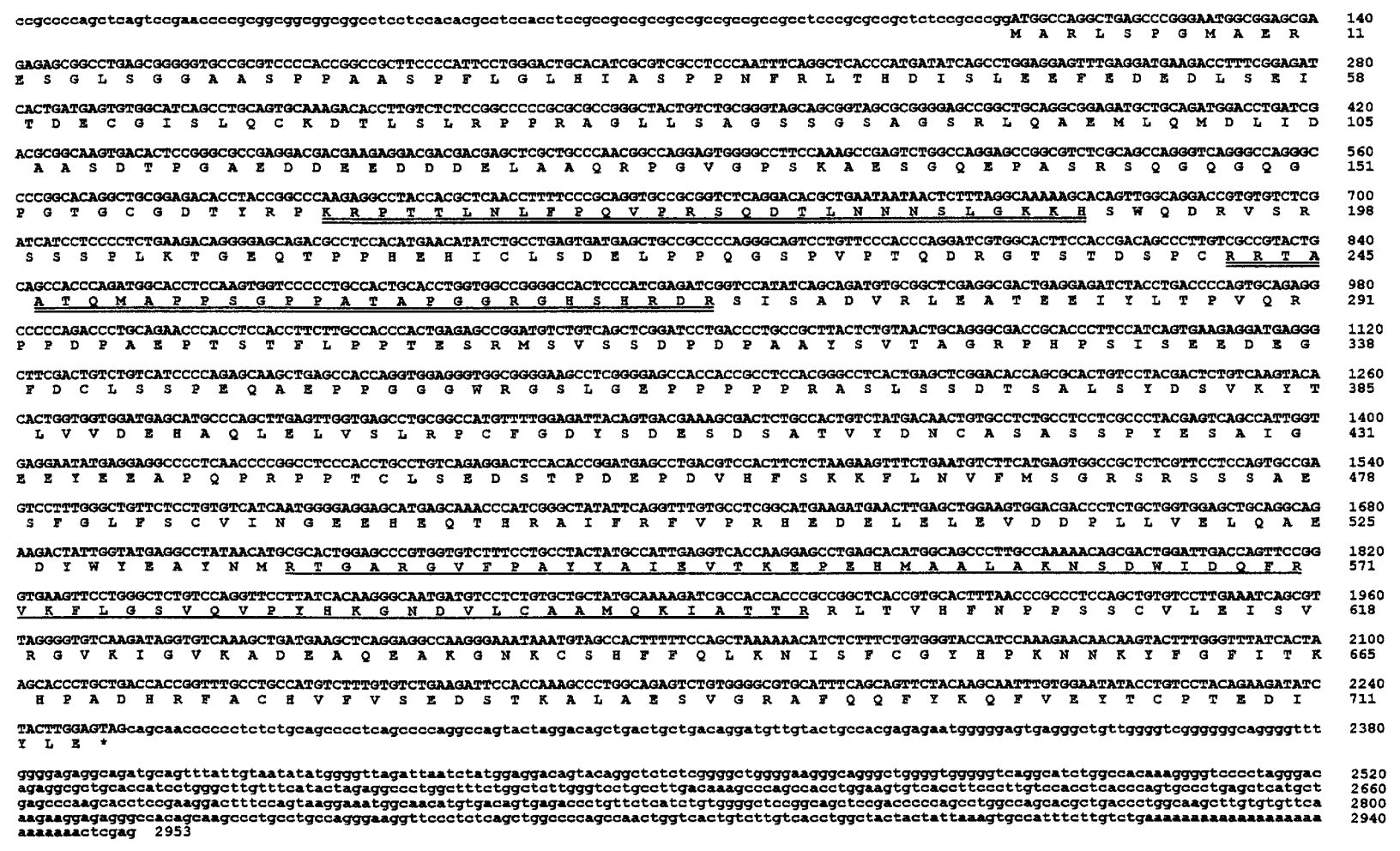

FIG. 1A. Nucleotide sequence of rat IB1 cDNA (SEQ ID NO:1) and its predicted amino acid sequence(SEQ ID NO:2). The nucleic acid residues are numbered from the nucleotide in the cDNA, and the amino acid residues are numbered from the beginning of the long open reading frame. Computer assisted analysis of the protein sequence indicates the presence of highly helicoidal structure (residues 31–61 and 114–125) and a proline-rich region (residues 292–366) in amino-terminal part of the protein, a putative nuclear localization signal (underlined twice) as well as a putative DNA-binding domain and bHLH dimerization domain (underlined once).

FIG 1B. Amino acid sequence comparison of IB1 (SEQ ID NO:13,14) with other bHLH proteins (SEQ ID NOS:15, 16,17,18,19,20,21,22,23,24). Amino acid sequence were aligned to maximize homology within the bHLH region. Shaded amino acids are conserved among bHLH proteins.

FIG. 1C. Partial cDNA sequence of human IB1 (SEQ ID NO:3).

FIG. 1D. Comparison of the rat IB1 (SEQ ID NOS:8,9, 10,11,12) translated amino acid sequence with the partial sequence obtained for human IB1 (SEQ ID NOS:4,5,6,7).

FIGS. 2A–2D

Tissue-specific Expression of IB1Gene.

Figure 2A:
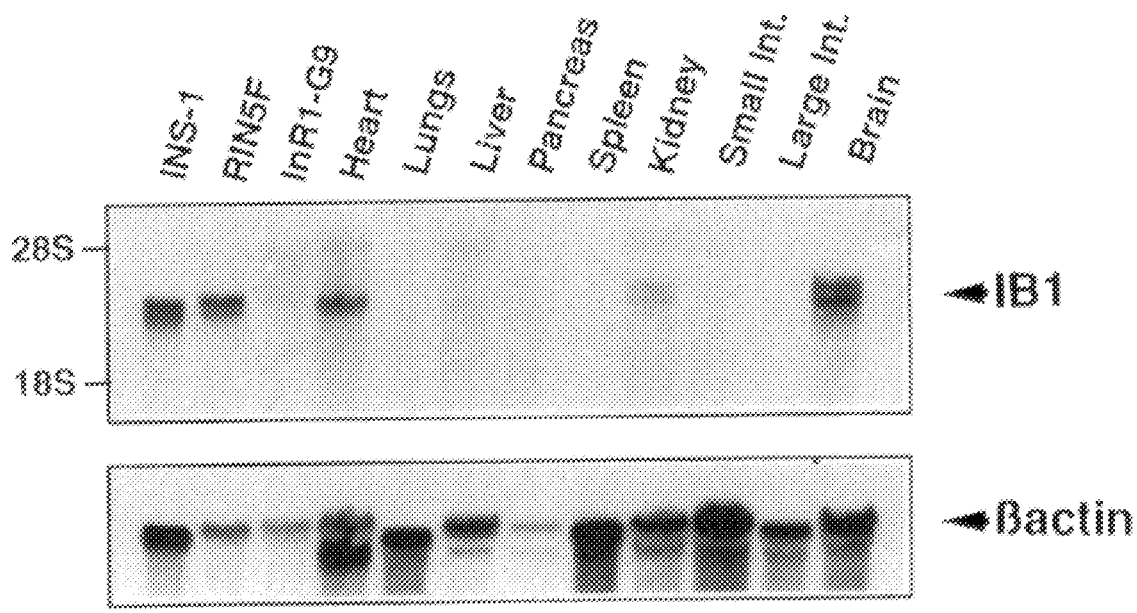

FIG. 2A. The distribution of IB1 transcript in tissues and cell lines was determined by Northern blot analysis using 10 μg of total RNA prepared from INS-1 and RIN5F (two insulin-producing β-cell lines), from InR1-G9 (a glucagon-producing α-cell line) and several rat tissues. IB1 transcripts of 3.0 and 3.2 kb were detected only in the insulin-secreting cell lines and in the brain and to a lower extent in the heart and kidney. The blot was stripped and rehybridized with a β-actin probe (bottom).

Figure 2B:
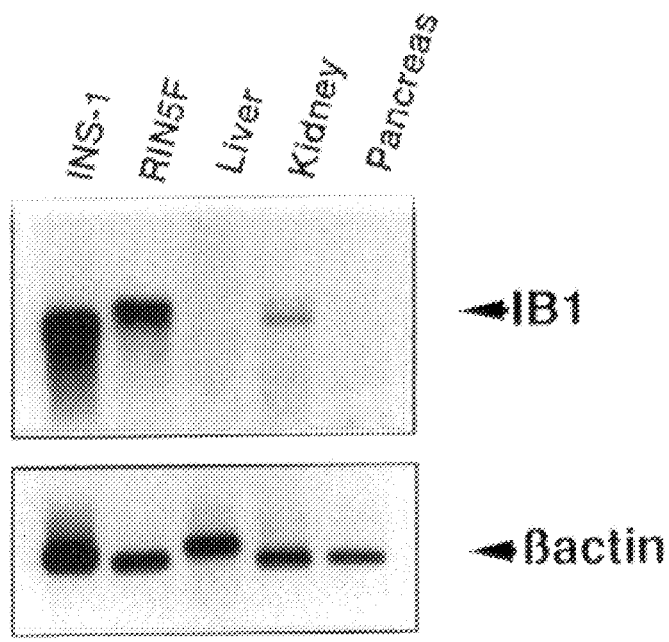

FIG. 2B. Five micrograms of poly(A+) RNA prepared from 2 differents insulin-secreting cell lines, from rat liver, kidney and pancreas were similarly analysed for IB1 gene expression. IB1 transcripts were detected in a cell- and tissue-specific manner.

FIG. 2C. A total of 5 μg of RNA obtained from isolated rat pancreatic islets incubated in 2.8 mM or 30 mM glucose for 14 hours were analyzed by Northern blotting together with rat liver and adipose tissue RNAs. IB1is abundantly expressed in the isolated islets and its expression is not regulated by glucose.

FIG. 2D. IB1gene expression in the rat brain. A total of 10 μg RNA extracted from the cortex (lane 1), pituitary gland (lane 2), hypothalamus (lane 3), cerebellum (lane 4) and medulla (lane 5) were separated in a formaldehyde gel and analyzed by Northern blot for IB1presence. The two IB1 transcripts were detected at high abundance in the cortex and the hypothalamus regions. The same blot was subsequently rehybridized with β-actin (bottom).

FIGS. 3A–3E

The IB1 Protein is Detected in Adult Rat Tissues.

Figure 3A:
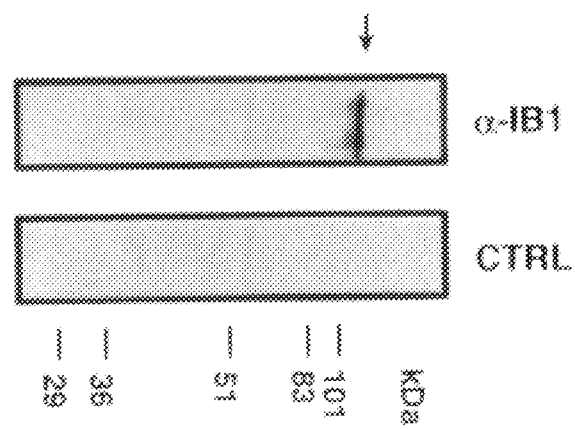

FIG. 3A. Immunoblot analysis of IB1. A rabbit polyclonal antibody (α-IB1) was raised towards the N-terminal part of the recombinant protein (a.a. 1–280) and affinity purified. Western blot analysis of βTC3 whole cell extracts with the α-IB1 antibody demonstrated the presence of a 120 kDa product which was undetected with the preimmune serum (CTRL).

Figure 3B:
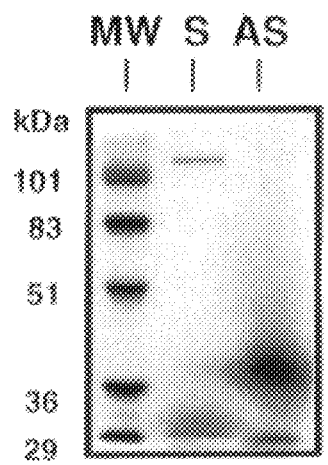

FIG. 3B. Determination of the apparent molecular weight of IB1. In vitro translated IB cDNA in the sense (S, T3 RNA-polymerase) or the antisense (AS, T7 RNA-polymerase) orientation in presence of $^{35}$S labelled methionine was separated by SDS-PAGE electrophoresis. An 120 kDA product is detected only in the cDNA translated in the sense orientation.

Figure 3C:
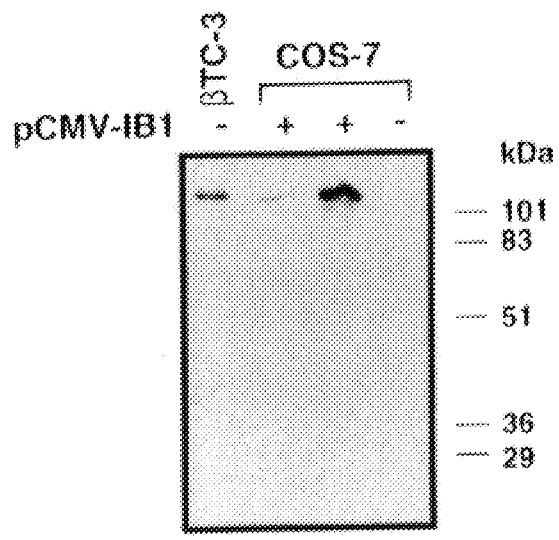

FIG. 3C. A plasmid containing the IB1 cDNA driven by a CMV promoter or its parent vector was transiently transfected into COS-7 cells and crude cellular extracts (20 μg) of these transfected cells analyzed by Western blotting. Using the α-IB1 antibodies, an approximatively 120 kDa protein was detected only in the transfected cells overexpressing IB1.

Figure 3D:
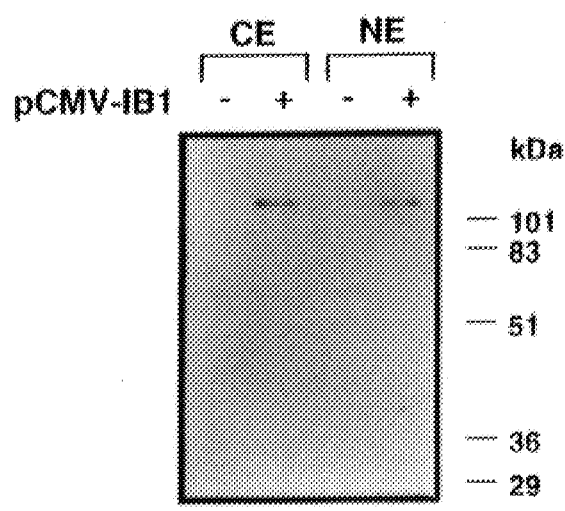

FIG. 3D. Similar experiments were carried out in transiently transfected COS-7 cells with the pCMV-IB1 vector and cytoplasmic (CE) or nuclear (NE) extracts prepared 48 hours after transfection. By Western blot analysis, IB1 is detected in the cytoplasm and the nucleus of the trasnfected cells.

Figure 3E:
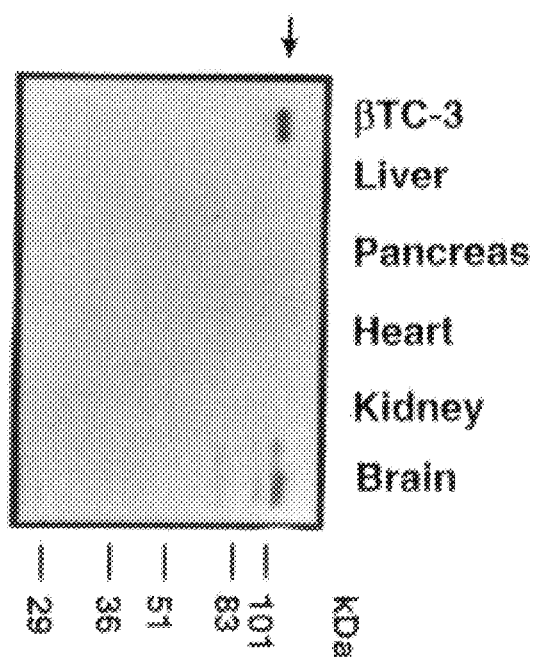

FIG. 3E. 20 μg of crude cellular extracts from several rat tissues and of the insulin-secreting β-cell line βTC3 were analysed by Western blotting using the α-IB1 antibodies. IB1 protein was detected in the brain and the insulin-secreting cell line.

FIGS. 4A–4I

Irnmunostaining Analysis of IB1 Expression.

FIG. 4A. Mouse pancreatic sections were immunostained with affinity purified α-IB1 antibodies and the detection was performed using a secondary avidin-biotin-peroxidase complex. IB1 staining is present in the cytoplasm and in the nuclei of the pancreatic islet cells but absent from the exocrine cells surrounding the islets.

FIG. 4B. GLUT2 immunostaining of similar pancreatic sections shows a typical staining of the cell membranes, different from the IB1localisation within the pancreatic islet.

FIG. 4C. A pancreatic islet immunostained with insulin antiserum which denotes a diffuse granular cytoplasmic staining.

FIG. 4D. Pre-immune antiserum against IB1 showed the absence of any staining in βTC3 cells.

FIGS. 4E–4F. Lower and larger magnification of βTC3 cells immunostained with α-IB1 antibodies. The protein is detected in the nuclei and in lower abundance in the cytoplasm of the cells.

Figure 4G:
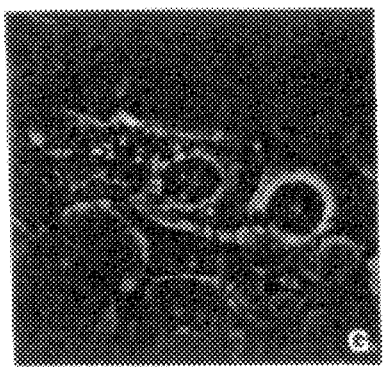

FIG. 4G. A plasmid containing a cDNA driven by a CMV promoter encoding a FLAG epitope together with the IB1 protein was transiently transfected into COS-7 cells (dark field photomicrograph).

Figure 4H:
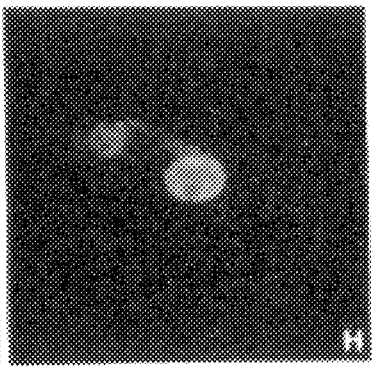

FIG. 4H. The FLAG epitope was detected by indirect immunofluorescence using an anti-FLAG antibody detected with a Texas-red labeled anti-mouse secondary antibody. The FLAG epitope is detected in the nucleus of the transfected COS cell.

Figure 4I:
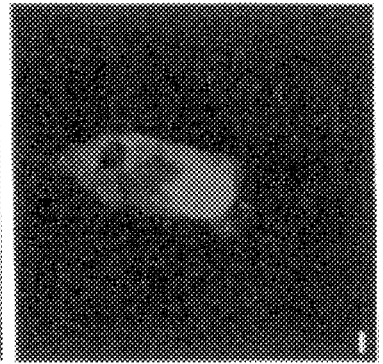

FIG. 4I. The same transfected COS-7 cells were immunodetected with the affinity purified α-IB1 antibody and a secondary anti-rabbit fluorescein-labeled antibody. IB1 protein is detected in the nucleus and the cytoplasm of the transfected COS-7 cells.

FIGS. 5A–5D

Similar DNA-binding Activity Between the GTII Cis Element of the GLUT2 Promoter and the Insulin Enhancer Sequence RIPE3.

Figure 5A:
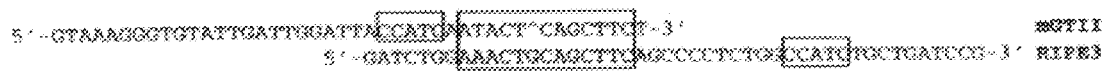

FIG. 5A. Nucleic acid sequences comparison between the murine GTII cis regulatory element (SEQ ID NO:25) and the rat insulin promoter element 3 (RIPE3) (SEQ ID NO:26). Some sequence identity is depicted and correspond, in part, to the RIPE3b element.

Figure 5B:
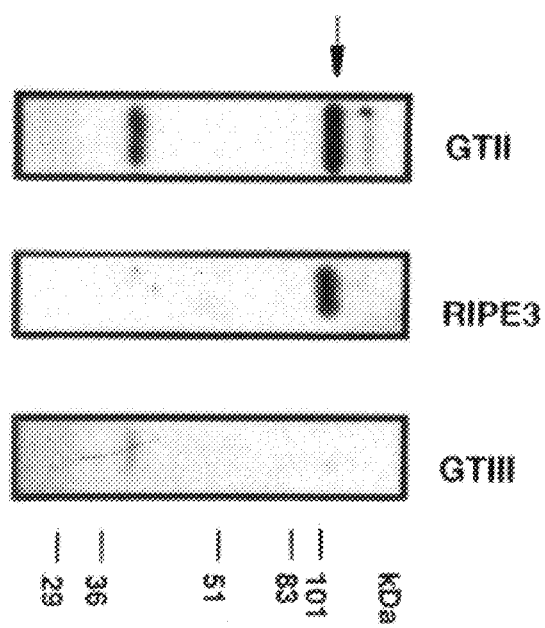

FIG. 5B. SouthWestern experiments were conducted using INS-1 nuclear extracts separated by SDS-PAGE gel electrophoresis and transferred to nitrocellulose membrane subsequently incubated with concatanated GTII, GTIII and RIPE3 labelled oligonucleotides. No specific binding was detected with the GTIII probe whereas the GTII and RIPE3 probes bind to an approximatively 120 kDa protein and with less specificity to a factor present at 40 kDA, also detectable with the GTIII probe.

Figure 5C:
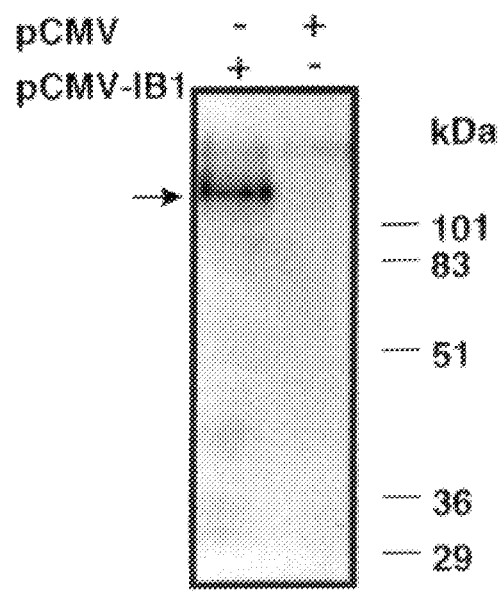

FIG. 5C. Plasmids containing the IB1 cDNA driven by a CMV promoter (pCMV-IB1) or its parent vector (pCMV) was transiently transfected into COS-7 cells and crude cellular extracts (20 μg) of these transfected cells were analysed by SouthWestern with the labeled GTII probe. The 120 kDA expressed protein is detected only in the transfected cells with the eukaryotic expression vector containing IB1cDNA.

Figure 5D:
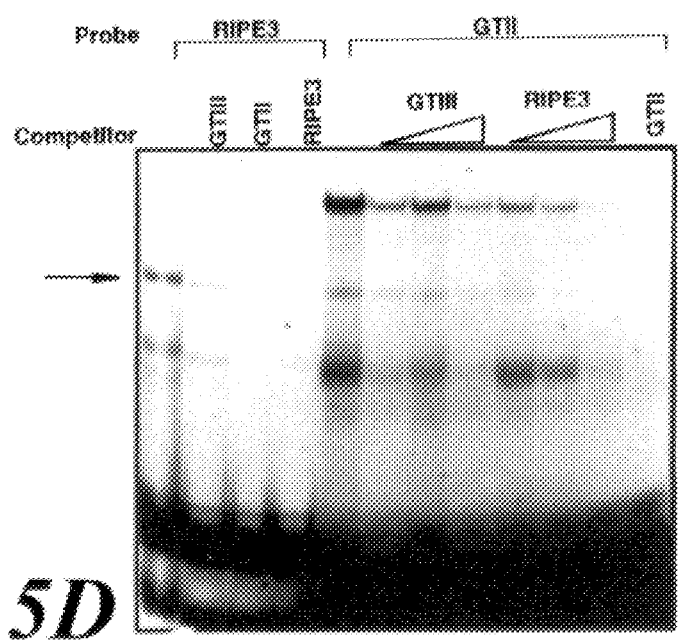

FIG. 5D. Gel retardation analysis conducted with the GTII and RIPE3 probes using βTC3 nuclear extracts. The RIPE3-binding activity is competed with an 100-fold excess of unlabelled RIPE3 or GTII oligonucleotides but not with an unrelated sequence (GTI). Conversely, the GTII-binding activity is competed with an 1000-fold excess of unlabeled RIPE3 oligonucleotides but not with an unrelated sequence (GTI).

FIGS. 6A–6C

Activation of the Insulin Enhancer Constructs and the GLUT2 Promoter by IB1

Figure 6A:
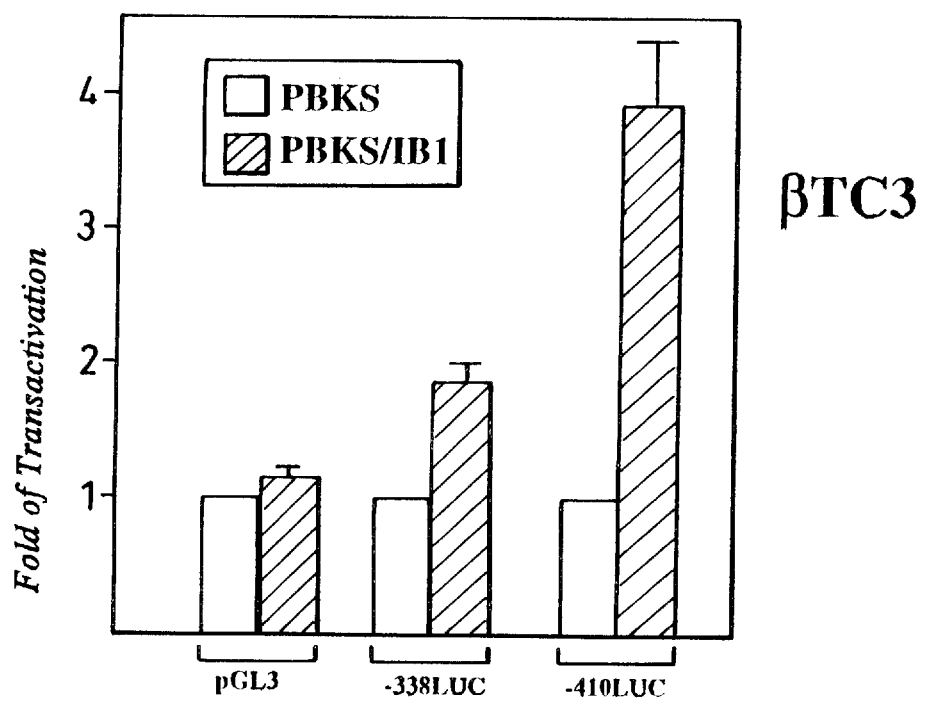
Figure 6A:
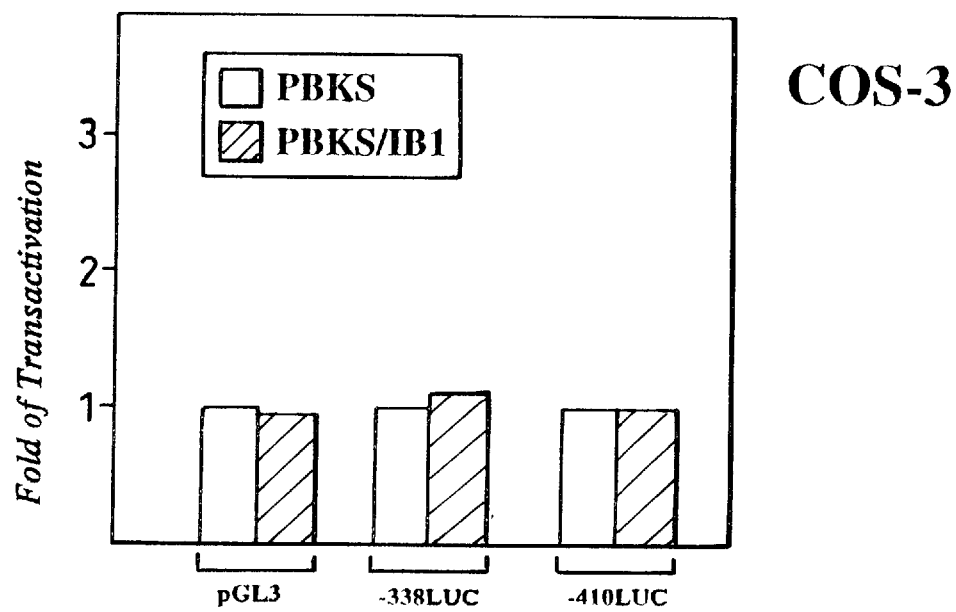

FIG. 6A. Two μg of the eukaryotic expression vector containing the IB1cDNA (PBKS/IB1) or its parent vector (PBKS) were transiently transfected into βTC3 cells together with 1 μg of the promoterless vector encoding the luciferase gene (pGL3) or −338 bp of the murine GLUT2 promoter cloned into the pGL3 vector (−338LUC) or −410 bp of the rat insulin I promoter similarly cloned into pGL3 (−410 LUC). IB1 transactivates the GLUT2 promoter (1.6±0.1 (SEM) over basal) but is a potent transactivator of the insulin promoter (3.8±0.8 (SEM) fold increase over basal). This effect is β-cell specific as it was not observed in a glucagon-producing cell line (InR1-G9, data not shown) or in an unrelated cells (COS-3).

Figure 6B:
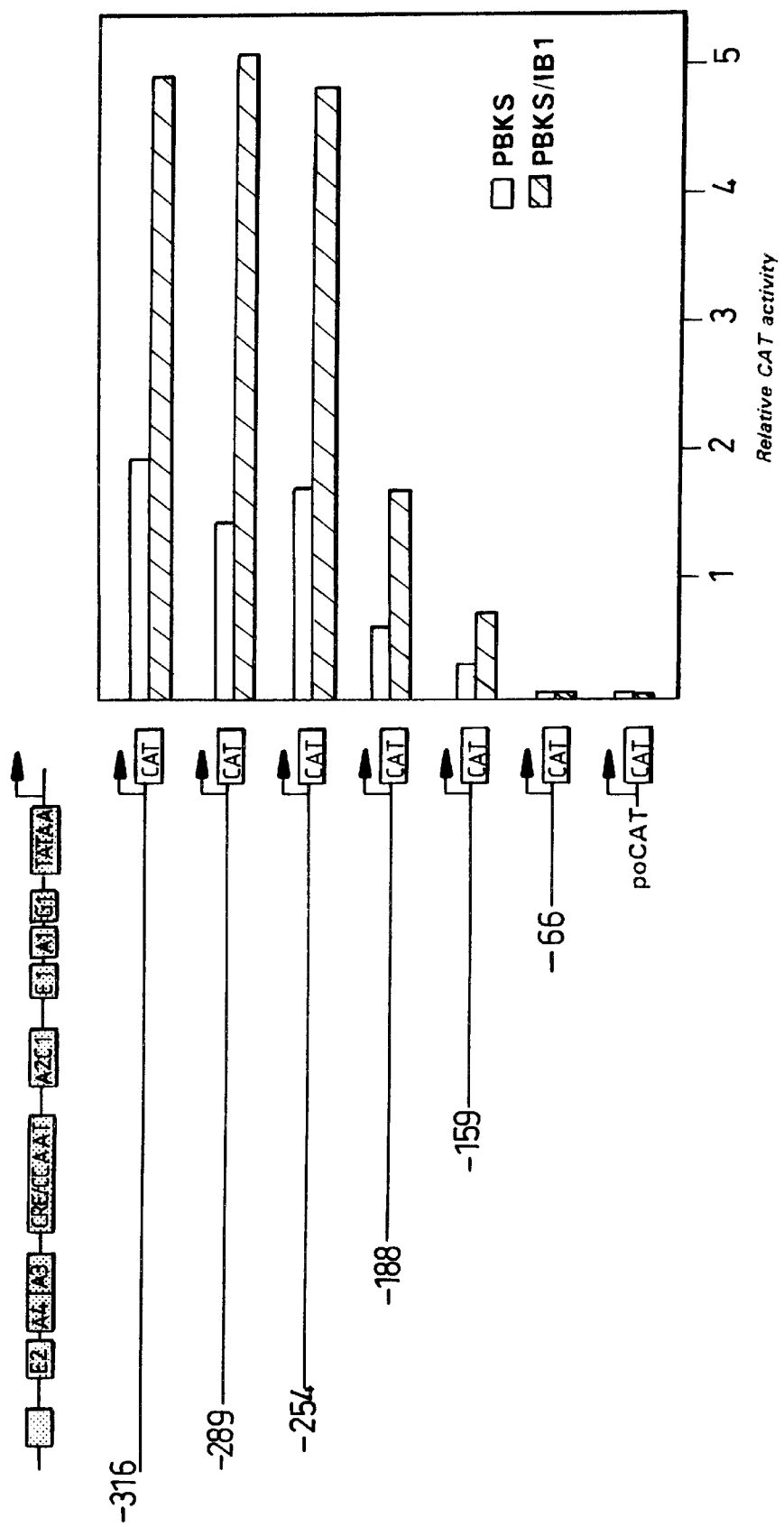

FIG. 6B. Several exonuclease III deletions constructs of the rat insulin promoter linked to a CAT reporter gene were transiently transfected into βTC3 cells in the presence of PBKS or PBKS/IB1. IB1 transactivated the insulin promoter and this effect was maximal within the −316 to −159 bp of the gene. Representative study done in duplicate in three independants experiments, normalized by protein content.

Figure 6C:
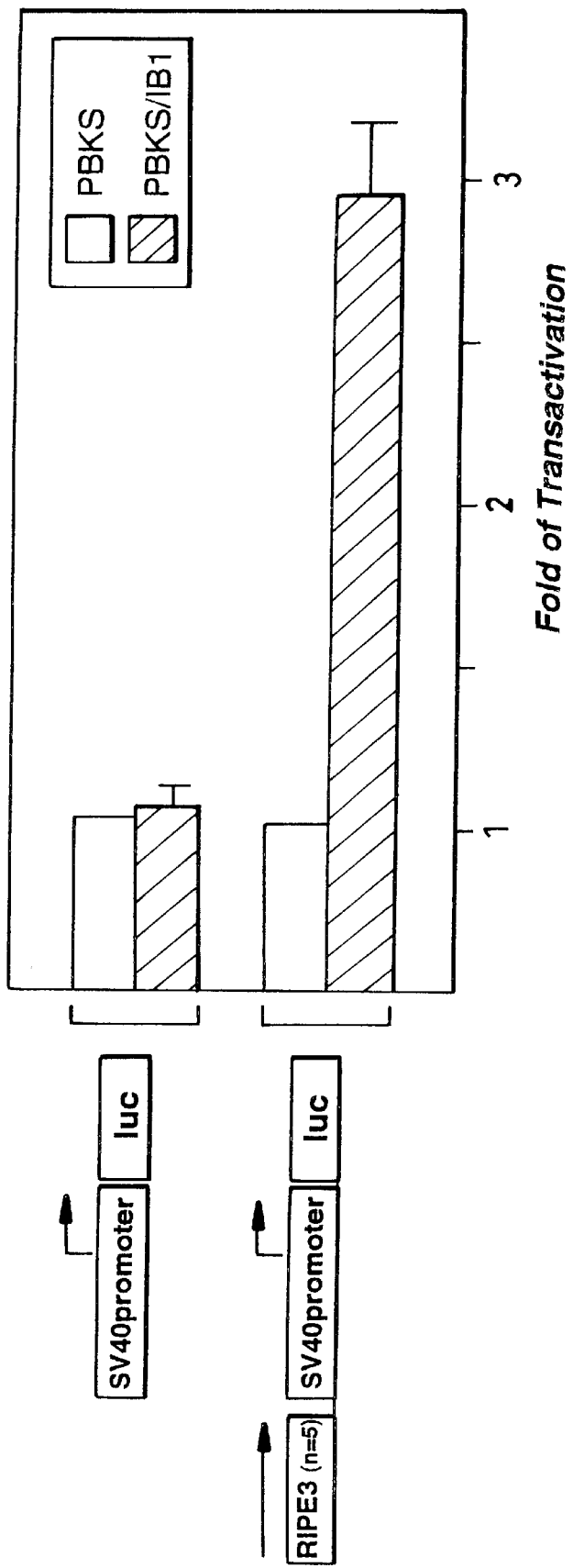

FIG. 6C. Five copies of the RIPE3 motif were multimerized 5' of a SV40 promoter linked to a luciferase reporter gene. This construct was transfected into βTC3 cells in the presence of the PBKS or the PBKS/IB1 construct. IB1 transactivated the RIPE3-luc construct in these cells (2.9±0.3 (SEM) fold increase over basal). Representative experiment done 12 times, in duplicate and normalized by protein content and/or the co-transfection of a HSK/TK-Renilla luciferase construct as internal control.

DETAILED DESCRIPTION

IB1 Nucleic Acid

"IB nucleic acid" includes a nucleic acid molecule which has a nucleotide sequence encoding a polypeptide which includes the amino acid sequence shown in FIG. 1A (SEQ ID NO:2) or 1D (SEQ ID NOS:4,5,6,7).

The IB1 coding sequence may be that shown in FIG. 1A (SEQ ID NO:1) or 1C (SEQ ID NO:3), or it may be a mutant, variant, derivative or allele of these sequences. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIG. 1A (SEQ ID NO:1) or 1C (SEQ ID NO:3) yet encode a polypeptide with the same amino acid sequence. The amino acid sequence of the complete rat IB1 polypeptide shown in FIG. 1A (SEQ ID NO:2) consists of 714 amino acids. The part of the human IB1 sequence shown in FIG. 1D (SEQ ID NO:4,5,6,7) consists of 270 amino acids and shares a 99% homology with the sequence of FIG. 1A (SEQ ID NO:2).

On the other hand, the encoded polypeptide may comprise an amino acid sequence which differs by one or more amino acid residues from the amino acid sequence shown in FIG. 1A or 1D (SEQ ID NO:2,4,5,6,7). Nucleic acid encoding a polypeptide which is an amino acid sequence mutant, variant, derivative or allele of the sequence shown in FIG. 1A or 1D (SEQ ID NO:2,4,5,6,7) is further provided by the present invention. Such polypeptides are discussed below. Nucleic acid encoding such a polypeptide may show greater than about 60% homology with the coding sequence shown in FIG. 1A or 1C (SEQ ID NO:1,3) greater than about 70% homology, greater than about 80% homology, greater than about 90% homology or greater than about 95% homology.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding all or part of the IB1 gene and/or its regulatory elements can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) amplification in E. coli. Modifications to the IB1 sequences can be made, e.g. using site directed mutagenesis, to lead to the expression of modified IB1 polypeptide or to take account of codon preference in the host cells used to express the nucleic acid.

In order to obtain expression of the IB1 nucleic acid sequences, the sequences can be incorporated in a vector having control sequences operably linked to the IB1 nucleic acid to control its expression. The vectors may include other sequences such as promoters or enhancers to drive the expression of the inserted nucleic acid, nucleic acid sequences so that the IB1 polypeptide is produced as a fusion and/or nucleic acid encoding secretion signals so that the polypeptide produced in the host cell is secreted from the cell. IB1 polypeptide can then be obtained by transforming the vectors into host cells in which the vector is functional, culturing the host cells so that the IB1 polypeptide is produced and recovering the IB1polypeptide from the host cells or the surrounding medium. Prokaryotic and eukaryotic cells are used for this purpose in the art, including strains of E. coli, yeast, and eukaryotic cells such as COS or CHO cells. The choice of host cell can be used to control the properties of the IB1 polypeptide expressed in those cells, e.g. controlling where the polypeptide is deposited in the host cells or affecting properties such as its glycosylation and phosphorylation.

PCR techniques for the amplification of nucleic acid are described in U.S. Pat. No. 4,683,195. In general, such techniques require that sequence information from the ends of the target sequence is known to allow suitable forward and reverse oligonucleotide primers to be designed to be identical or similar to the polynucleotide sequence that is the target for the amplification. PCR comprises steps of denaturation of template nucleic acid (if double-stranded), annealing of primer to target, and polymerisation. The nucleic acid probed or used as template in the amplification reaction may be genomic DNA, cDNA or RNA. PCR can be used to amplify specific sequences from genomic DNA, specific RNA sequences and cDNA transcribed from mRNA, bacteriophage or plasmid sequences. The IB1 nucleic acid sequences provided herein readily allow the skilled person to design PCR primers. References for the general use of PCR techniques include Mullis et al, Cold Spring Harbor Symp. Quant. Biol., 51:263, (1987), Ehrlich (ed), PCR Technology, Stockton Press, N.Y., 1989, Ehrlich et al, Science, 252:1643–1650, (1991), "PCR protocols; A Guide to Methods and Applications", Eds. Innis et al, Academic Press, New York, (1990).

Also included within the scope of the invention are antisense oligonucleotide sequences based on the IB1 nucleic acid sequences described herein, particularly to block the synthesis of IB1 in situation where IB1 overexpression has a deleterious effect such as the dementia associated with Parkinson's disease. Antisense oligonucleotides may be designed to hybridise to the complementary sequence of nucleic acid, pre-mRNA or mature mRNA, interfering with the production of polypeptide encoded by a given DNA sequence (e.g. either native IB1 polypeptide or a mutant form thereof), so that its expression is reduce or prevented altogether. In addition to the IB1 coding sequence, antisense techniques can be used to target the control sequences of the IB1 gene, e.g. in the 5' flanking sequence of the IB1 coding sequence, whereby the antisense oligonucleotides can interfere with IB1 control sequences. The construction of antisense sequences and their use is described in Peyman and Ulman, Chemical Reviews, 90:543–584, (1990), Crooke, Ann. Rev. Pharmacol. Toxicol., 32:329–376, (1992), and Zamecnik and Stephenson, P.N.A.S, 75:280–284, (1974).

The nucleic acid sequences provided in FIGS. 1A and 1C (SEQ ID NO:1,3) are useful for identifying nucleic acid of interest (and which may be according to the present invention) in a test sample. The present invention provides a method of obtaining nucleic acid of interest, the method including hybridisation of a probe having the sequence shown in FIG. 1A or 1C (SEQ ID NO:1,3) or a complementary sequence, to target nucleic acid.

Hybridisation is generally followed by identification of successful hybridisation and isolation of nucleic acid which has hybridised to the probe, which may involve one or more steps of PCR.

Nucleic acid according to the present invention is obtainable using one or more oligonucleotide probes or primers designed to hybridise with one or more fragments of the nucleic acid sequence shown in FIG. 1A or 1C (SEQ ID NO:1,3), particularly fragments of relatively rare sequence, based on codon usage or statistical analysis. A primer designed to hybridise with a fragment of the nucleic acid sequence shown in the above figures may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with the sequence shown in FIG. 1A or 1C and a primer which hybridises to the oligonucleotide linker. These techniques can be used to isolate clones containing the complete human IB1 nucleic acid sequence which can then be sequenced using techniques well known in the art.

Such oligonucleotide probes or primers, as well as the full-length sequence (and mutants, alleles, variants and derivatives) are also useful in screening a test sample containing nucleic acid for the presence of alleles, mutants and variants, especially those that lead to the production of inactive forms of IB1 protein, the probes hybridising with a target sequence from a sample obtained from the individual being tested. The conditions of the hybridisation can be controlled to minimise non-specific binding, and preferably stringent to moderately stringent hybridisation conditions are preferred. The skilled person is readily able to design such probes, label them and devise suitable conditions for the hybridisation reactions, assisted by textbooks such as Sambrook et al (1989) and Ausubel et al (1992).

As well as determining the presence of polymorphisms or mutations in the IB1 sequence, the probes may also be used to determine whether mRNA encoding IB1 is present in a cell or tissue.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR). Thus, the IB1 nucleic acid sequences disclosed herein can be used to isolate genes from other species, especially from the two human IB1 genes, the partial sequences of which are shown in FIG. 1C. The genes are located on chromosomes 17 (17q21–22) and 11 (11p11), the first gene being intronless and the second containing multiple exons. Both genes appear to be functional. Polymorphisms within them may be used as markers for human genetic diseases such as diabetes, and neurological disorders including dementia, neurodegenerative disease and/or parkinsonism.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAse cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions, nucleic acid libraries, e.g. cDNA libraries representative of expressed sequences, may be searched.

Those skilled in the art are well able to employ suitable conditions of the desired stringency for selective hybridisation, taking into account factors such as oligonucleotide length and base composition, temperature and so on.

On the basis of amino acid sequence information, oligonucleotide probes or primers may be designed, taking into account the degeneracy of the genetic code, and where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18–20. Those skilled in the art are well versed in the design of primers for use processes such as PCR.

A further aspect of the present invention provides an oligonucleotide or polynucleotide fragment of the nucleotide sequence shown in FIG. 1A or 1C, or a complementary sequence, in particular for use in a method of obtaining and/or screening nucleic acid. The sequences referred to above may be modified by addition, substitution, insertion or deletion of one or more nucleotides, but preferably without abolition of ability to hybridise selectively with nucleic acid with the sequence shown in FIG. 1A or 1C, that is wherein the degree of homology of the oligonucleotide or polynucleotide with one of the sequences given is sufficiently high.

In some preferred embodiments, oligonucleotides according to the present invention that are fragments of any of the sequences shown in FIG. 1A or 1C, or an allele thereof, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of susceptibility to diabetes, parkinsonism and/or dementia.

Nucleic acid according to the present invention may be used in methods of gene therapy, for instance in treatment of individuals with the aim of preventing or curing (wholly or partially) the above mentioned conditions. This too is discussed below.

A convenient way of producing a polypeptide according to the present invention is to express nucleic acid encoding it, by use of the nucleic acid in an expression system. The use of expression system has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extrachromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid may take place in vivo by way of gene therapy, as discussed below.

A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) The presence of a mutant, allele or variant sequence within cells of an organism, particularly when in place of a homologous endogenous sequence, may allow the organism to be used as a model in testing and/or studying the role of the IB1 gene or substances which modulate activity of the encoded polypeptide in vitro.

Instead of or as well as being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as DHFR. Host cells transformed with nucleic acid of interest, or which are descended from host cells into which nucleic acid was introduced, may be cultured under suitable conditions, e.g. in a fermenter, taken from the culture and subjected to processing to purify the nucleic acid. Following purification, the nucleic acid or one or more fragments thereof may be used as desired, for instance in a diagnostic or prognostic assay as discussed elsewhere herein.

IB1Proteins

The term "IB-1 biological activity" is herein defined as binding to nucleic acid defining the GTII or RIPE3 and transactivating the GLUT2 or insulin promoter and/or interacting with other proteins. Experiments to determine these activities are described in detail below.

The skilled person can use the techniques described herein and others well known in the art to produce large amounts of the IB1 polypeptide, or fragments or active portions thereof, for use as pharmaceuticals, in the developments of drugs and for further study into its properties and role in vivo.

Thus, a further aspect of the present invention provides a polypeptide which has the amino acid sequence shown in FIG. 1A or 1C, which may be in isolated and/or purified form, free or substantially free of material with which it is naturally associated, such as other polypeptides or such as human polypeptides other than IB1 polypeptide or (for example if produced by expression in a prokaryotic cell) lacking in native glycosylation, e.g. unglycosylated.

Polypeptides which are amino acid sequence variants, alleles, derivatives or mutants are also provided by the present invention. A polypeptide which is a variant, allele, derivative or mutant may have an amino acid sequence which differs from that given in FIG. 1A or 1C by one or more of addition, substitution, deletion and insertion of one or more amino acids. Preferred such polypeptides have IB1 function, that is to say they activate the GLUT2 or insulin promoters, leading to production of GLUT2 protein or insulin. Preferably, this activation is specific to insulin-secreting cells and does not take place in non-pacreatic or glucagon producing cells.

A polypeptide which is an amino acid sequence variant, allele, derivative or mutant of the amino acid sequence shown in FIG. 1A or 1C may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. The sequence may share greater than about 60% similarity, greater than about 70% similarity, greater than about 80% similarity or greater than about 90% similarity with the amino acid sequence shown in FIG. 1A or 1C. Particular amino acid sequence variants may differ from those shown in FIG. 1A or 1C by insertion, addition, substitution or deletion of 1 amino acid, 2, 3, 4, 5–10, 10–20 20–30, 30–50, 50–100, 100–150, or more than 150 amino acids.

By way of example, screening for mutation variants in a test sample has a diagnostic and/or prognostic use, for instance in determining susceptibility to diabetes, parkinsonism and/or dementia, as discussed below.

The present invention also includes active portions, fragments, derivatives and functional mimetics of the IB1 polypeptides of the invention.

An "active portion" of IB1 polypeptide means a peptide which is less than said full length IB1 polypeptide, but which retains at least some of its essential biological activity. For instance, smaller fragments of IB1 could act as sequestrators by interacting with other proteins.

A "fragment" of the IB1 polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the IB1 polypeptide sequence antigenic determinants or epitopes useful for raising antibodies to a portion of the IB1 amino acid sequence.

A "derivative" of the IB1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the wild type IB1 polypeptide.

"Functional mimetic" means a substance which may not contain an active portion of the IB1 amino acid sequence, and probably is not a peptide at all, but which retains the essential biological activity of natural IB1 polypeptide. The design and screening of candidate mimetics is described in detail below.

A polypeptide according to the present invention may be isolated and/or purified (e.g. using an antibody) for instance after production by expression from encoding nucleic acid (for which see below). Polypeptides according to the present invention may also be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide fragment, allele, mutant or variant according to the present invention may be used as an immunogen or otherwise in obtaining specific antibodies. Antibodies are useful in purification and other manipulation of polypeptides and peptides, diagnostic screening and therapeutic contexts. This is discussed further below.

A polypeptide according to the present invention may be used in screening for molecules which affect or modulate its activity or function. Such molecules may be useful in a therapeutic (possibly including prophylactic) context.

The IB1polypeptides can also be linked to effector molecules such as labels, drugs and/or transport molecules such as the Penentratin peptide described in WO 91/19981.

Antibodies

A further important use of the IB1 polypeptides is in raising antibodies that have the property of specifically binding to the IB1 polypeptides, or fragments or active portions thereof. As mentioned above, anti-IB1 antiserum was prepared against recombinant IB1 (amino acids 1–280). These antibodies were raised in a rabbit and are polyclonal. The antibodies were affinity purified and are useful tools as they can recognise IB1 epitope(s). These and other antibodies that can be made based on the disclosure herein can be used as a diagnostic tools and in the characterisation of IB1.

It is possible to produce monoclonal antibodies to IB1 protein and the techniques for doing this are well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

The provision of the novel IB1 polypeptides enables for the first time the production of antibodies able to bind it specifically. Accordingly, a further aspect of the present invention provides an antibody able to bind specifically to the polypeptide whose sequence is given in FIG. 1A or 1C. Such an antibody may be specific in the sense of being able to distinguish between the polypeptide it is able to bind and other human polypeptides for which it has no or substantially no binding affinity (e.g. a binding affinity of about 1000×worse) . Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type IB1 polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser exciting dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Diagnostic Methods

A number of methods are known in the art for analysing biological samples from individuals to determine whether the individual carries a IB1allele predisposing them to diabetes, dementia and/or parkinsonism. The purpose of such analysis may be used for diagnosis or prognosis, to assist a physician in determining the severity or likely course of the condition and/or to optimise treatment of it. Alternatively, the methods can be used to detect IB1 alleles that are statistically associated with a susceptibility to these conditions in the future, e.g. identifying individuals who would benefit from regular screening.

Broadly, the methods divide into those screening for the presence of IB1 nucleic acid sequences and those that rely on detecting the presence or absence of the IB1 polypeptide. The methods make use of biological samples from individuals that are suspected of contain the nucleic acid sequences or polypeptide. Examples of biological samples include blood, plasma, serum, tissue samples, tumour samples, saliva and urine.

Exemplary approaches for detecting IB1 nucleic acid or polypeptides include:

(a) comparing the sequence of nucleic acid in the sample with the IB1 nucleic acid sequence to determine whether the sample from the patient contains mutations; or, (b) determining the presence in a sample from a patient of the polypeptide encoded by the IB1 gene and, if present, determining whether the polypeptide is full length, and/or is mutated, and/or is expressed at the normal level; or, (c) using DNA fingerprinting to compare the restriction pattern produced when a restriction enzyme cuts a sample of nucleic acid from the patient with the restriction pattern obtained from normal IB1 gene or from known mutations thereof; or, (d) using a specific binding member capable of binding to a IB1 nucleic acid sequence (either a normal sequence or a known mutated sequence), the specific binding member comprising nucleic acid hybridisable with the IB1 sequence, or substances comprising an antibody domain with specificity for a native or mutated IB1 nucleic acid sequence or the polypeptide encoded by it, the specific binding member being labelled so that binding of the specific binding member to its binding partner is detectable; or, (e) using PCR involving one or more primers based on normal or mutated IB1gene sequence to screen for normal or mutant IB1 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, molecules and receptors and complementary nucleotide sequences. The skilled person will be able to think of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridise to each other under the conditions of the assay, preferably greater than 10 nucleotides long, more preferably greater than 15 or 20 nucleotides long.

In most embodiments for screening for IB1 susceptibility alleles, the IB1 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

A variant form of the IB1 gene may contain one or more insertions, deletions, substitutions and/or additions of one or more nucleotides compared with the wild-type sequence which may or may not disrupt the gene function. Differences at the nucleic acid level are not necessarily reflected by a difference in the amino acid sequence of the encoded polypeptide, but may be linked to a known dysfunction. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript.

There are various methods for determining the presence or absence in a test sample of a particular nucleic acid sequence, such as the sequence shown in FIG. 1A or 1C (SEQ ID NO:1,3) or a mutant, variant or allele thereof.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RNAses.

Nucleic acid in a test sample may be sequenced and the sequence compared with the sequence shown in FIG. 1A or 1C (SEQ ID NO:1,3), to determine whether or not a difference is present. If so, the difference can be compared with known susceptibility alleles to determine whether the test nucleic acid contains one or more of the variations indicated.

Since it will not generally be time- or labour-efficient to sequence all nucleic acid in a test sample or even the whole IB1 gene, a specific amplification reaction such as PCR using one or more pairs of primers may be employed to amplify the region of interest in the nucleic acid, for instance the IB1 gene or a particular region in which mutations associated with a susceptibility to one of the conditions mentioned above. The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the IB1 gene, or its complement, containing a sequence alteration known to be associated with a susceptibility to the conditions mentioned above. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Use of oligonucleotide probes and primers has been discussed in more detail above.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RNAse A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal IB1 gene (either sense or anti-sense strand) in which mutations are known to occur may be annealed to test nucleic acid and the presence or absence of a mis-match determined. Detection of the presence of a mis-match may indicate the presence in the test nucleic acid of a mutation. On the other hand, an oligonucleotide probe that has the sequence of a region of the IB1 gene including a mutation may be annealed to test nucleic acid and the presence or absence of a mis-match determined. The absence of a mis-match may indicate that the nucleic acid in the test sample has the normal sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence or the absence of an important regulatory element in a promoter or other regulatory sequence located in introns may also be assessed by determining the level of mRNA production by transcription or the level of polypeptide production by translation from the mRNA.

A test sample of nucleic acid may be provided for example by extracting nucleic acid from cells, e.g. in saliva or preferably blood, or for pre-natal testing from the amnion, placenta or foetus itself.

There are various methods for determining the presence or absence in a test sample of a particular polypeptide, such as the polypeptide with the amino acid sequence shown in FIG. 1A or 1C or an amino acid sequence mutant, variant or allele thereof.

A sample may be tested for the presence of a binding partner for a specific binding member such as an antibody (or mixture of antibodies), specific for one or more particular variants of the polypeptide shown in FIG. 1A or 1C.

A sample may be tested for the presence of a binding partner for a specific binding member such as an antibody (or mixture of antibodies), specific for the polypeptide shown in FIG. 1A or 1C (SEQ ID NO:1,3).

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the polypeptide whose sequence is shown in FIG. 1A or 1C (SEQ ID NOS: 1,3), or if it is a mutant or variant form. Amino acid sequence is routine in the art using automated sequencing machines.

Therapeutics

Pharmaceuticals and Peptide Therapies

The IB1polypeptides, antibodies, peptides and nucleic acid of the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed) , 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated.
Methods of Gene Therapy As a further alternative, the nucleic acid encoded the authentic biologically active IB1 polypeptide could be used in a method of gene therapy, to treat a patient who is unable to synthesize the active polypeptide or unable to synthesize it at the normal level, thereby providing the effect provided by wild-type IB1 and suppressing the occurrence of diabetes in the target cells.

Vectors such as viral vectors have been used in the prior art to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding the IB1 polypeptide, or an active portion thereof, is to increase the amount of the expression product of the nucleic acid in cells in which the level of the wild-type IB1 polypeptide is absent or present only at reduced levels. Target cells for gene therapy include insulin secreting β-cells or any neuron derived cells. Cell engineering can be used to provide the overexpression or repression of IB1 in transfected cell lines which can then be subsequently transplanted to humans. Gene therapy can be employed using a promoter to drive IB1 expression in a tissue specific manner (i.e. an insulin promoter linked to IB1 cDNA will overexpress IB1 in β-cells and transiently in the brain). If defective function of IB1 is involved in neurological disease, IB1 can be overexpressed in transformed cell lines for transplantation.

Gene transfer techniques which selectively target the IB1 nucleic acid to breast and/or ovarian tissues are preferred. Examples of this included receptor-mediated gene transfer, in which the nucleic acid is linked to a protein ligand via polylysine, with the ligand being specific for a receptor present on the surface of the target cells.

Antisense technology based on the IB1 nucleic acid sequences is discussed above.
Methods of Screening for Drugs A polypeptide according to the present invention may be used in screening for molecules which affect or modulate its activity or function. Such molecules may be useful in a therapeutic (possibly including prophylactic) context.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred.

Prior to or as well as being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide. Alternatively, the screen could be used to screen test substances for binding to a IB1 specific binding partner, to find mimetics of the IB1polypeptide, e.g. for testing as therapeutics.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition to a patient, e.g. for treatment (which may include preventative treatment) of diabetes, use of such a substance in manufacture of a composition for administration, and a method of making a pharmaceutical composition comprising admixing such a substance with a pharmaceutically acceptable excipient, vehicle or carrier, and optionally other ingredients.

A substance identified using as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore".

Once the pharmacophore has been found, its structure is modelled to according its physical properties, eg stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

Screening for Substances Affecting IB1 Expression

The present invention also provides the use of all or part of the nucleic acid sequence of the IB1 promoter in methods of screening for substances which modulate the activity of the promoter and increase or decrease the level of IB1 expression.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

Further provided by the present invention is a nucleic acid construct comprising a IB1 promoter region set out in FIG. 6 or a fragment, mutant, allele, derivative or variant thereof able to promoter transcription, operably linked to a heterologous gene, e.g. a coding sequence. A "heterologous" or "exogenous" gene is generally not a modified form of IB1 Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Nucleic acid constructs comprising a promoter (as disclosed herein) and a heterologous gene (reporter) may be employed in screening for a substance able to modulate activity of the promoter. For therapeutic purposes, e.g. for treatment of diabetes a substance able to up-regulate expression of the promoter directing the expression of normal may be sought. Alternatively, substances to down-regulate the promoter may help to prevent or inhibit the production of mutated IB1 polypeptide, if this is an agent implicated in the development of diabetes. A method of screening for ability of a substance to modulate activity of a promoter may comprise contacting an expression system, such as a host cell, containing a nucleic acid construct as herein disclosed with a test or candidate substance and determining expression of the heterologous gene.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the promoter.

A promoter construct may be introduced into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug. These may be administered to individuals.

Materials and Methods
Construction of an INS-1 cDNA Expression Library and Cloning of the IB1 cDNA.

An oligo(dT)-primed cDNA was generated from 10 $\mu$g of poly(A)$^+$ RNA obtained from the differentiated INS-1 insulin secreting cell line using a cDNA synthesis kit (Stratagene, La Jolla, Calif.) according to the manufacturer's instructions. The cDNAs were cloned into the EcoRI and XhoI sites of the LambdaZap Express expression vector (Stratagene, La Jolla, Calif.). A total of 2×10$^6$ colonies were screened by the procedure described by Singh et al (38) using as probe concatanated GTII oligonucleotides. 5 $\mu$g of double stranded GTII oligonucleotides (5'-GTAAAGGGTGTATTGATTGGATTACCATCAATACTC AGCTTCT-3') (SEQ ID NO:25) were filled in by the Klenow fragment of DNA polymerase I in the presence of ($\alpha^{32}$P)deoxycytosine-triphosphate and the free nucleotides separated through a G-50 spun column. These labelled oligonucleotides were subsequently ligated to generate the concatanated probe. The expression cloning was performed exactly as previously described for the SouthWestern experiments, except that we used 10 ug/ml of single stranded DNA in place of poly dI/dC in a total reaction volume of 250 ml(3). One IB1 positive clone was obtained from the screening and the cDNA sequenced in both 5' and 3' orientations.

Cell Lines

The transplantable X-ray induced rat insulinoma INS-1 cell line was provided by Asfari et al. and grown as described (1). The mouse insulin-producing $\beta$TC3 cell line, the hamster glucagon-producing InR1-G9 cells and the kidney-derived COS-7 cell line were cultured in RPMI 1640 medium containing 10% fetal calf serum, 2 mM L-glutamine, 100 U/ml penicillin and 100 mg/ml streptomycin(9,40).

Plasmid Constructions, Transient Transfections, CAT and Luciferase Assays.

The eukaryotic expression vector encoding IB1 was constructed by inserting the IB1 cDNA in the NheI/XhoI sites of the CMV-driven plasmid PBKS (Stratagene, La Jolla, Calif.) to generate the PBKS-IB1 vector. PCR mutagenesis was used to add a FLAG epitope (Kodak, New Haeven,CT) just C-terminal of the initiating methionine of the IB1 cDNA in the PBKS-IB1 construct. Dideoxy sequencing of the resulting plasmids was used to confirm the correct sequence of the clones thus obtained. The −410 bp of the rat insulin II promoter and the −338 bp of the murine GLUT2 promoter were cloned 5' of the luciferase gene of the pGL3Basic vector (Promega, Madison,Wis.). The RIPE3 double-stranded oligonucleotides (5-GATCTGGAAACT GCAGCTTCAGCCCCTCTGGCCATCTGCTGATCCG-3') (SEQ ID NO:26) were multimerized, filled-in by Klenow, and blunt-end ligated into the SmaI site of the SV40 early minimal promoter linked to a luciferase gene (pGL3 promoter, Promega). The five copies of the RIPE3 element cloned into pGL3promoter were sequenced. The −316, −289, −254, −188, −159 and −66 bp of the rat I insulin promoter linked to the CAT reporter gene were kindly provided by Jacques Philippe from the University Medical School of Geneva.

All constructs were transiently transfected using the cationic reagent DOTAP in solution as recommended by the supplier (Boehringer Mannheim). Two $\mu$g of the reporter DNAs (luciferase or CAT constructs) with 1 $\mu$g of transactivator (PBKS or PBK/IB1) were used for 1–2×10$^6$ cells and incubated for 48–56 hours. In some transfection experiments, co-transfection with 500 ng of the herpes simplex virus thymidine kinase (HSV-TK) promoter driving the Renilla luciferase gene (Promega, Madison,Wis.) were included in order to control the transfection efficiency. The transfected cells were harvested with Promega lysis buffer, the cellular debris removed, and the supernatant collected. Protein concentrations were determined using the Bio-Rad protein assay (Bio-Rad Laboratories, Richmond, Cilif.). Luciferase activities were measured twice with 50 to 100 $\mu$g of protein extracts from each transfected plate according to the protocol of Brasier et al(4).

Gel Shift Assays and SouthWestern Experiments.

Nuclear and cytoplasmic extracts were prepared according to the method of Dent and Latchmann (7). The sequences of the oligonucleotides GTII and RIPE3 are described above. Complementary sense and antisense oligonucleotides were hybridized and then filled in by the Klenow fragment of DNA polymerase I in the presence of ($\alpha$32P) deoxycytosine triphosphate. The end-labelled probe was incubated with 2 $\mu$g nuclear extracts exactly as described previously for the band shift assays (3). The SouthWestern experiments were conducted as described with the modifications detailed above (3). The in vitro translation experiments were conducted using the coupled translation-traduction kit (TNT) from Promega (Madison, Wis.) and according to the manufacturer's instructions in the presence of ($^{35}$S) methionine. The labelled protein was resolved by PAGE on a 10% SDS-containing gel.

RNA and Northern Blot Analysis

The RNA isolation and Northern blot analysis from rat tissues or cell lines were conducted exactly as previously described (3). The rat pancreatic islets were isolated by the method of Gotoh et al (15).

Preparation of Antisera.

Anti-IB1 antiserum was prepared using a cDNA fragment encoding the first 280 amino acids of the protein. This fragment was inserted into the His-tagged pQE-9 expression vector (Quiagen, Basel, Switzerland), expressed and subsequently purified through a $Ni^{2+}$-containing column following instructions from the manufacturer (Quiagen, Basel, Switzerland) and used to elicit polyclonal antibodies in rabbits. To affinity-purified the antibodies, the $Ni^{2+}$-column purified 1–280 a.a. of the recombinant protein was immobilized onto a nitrocellulose membrane and the rabbit serum purified by several steps of incubation with this membrane in PBS (phosphate-buffered saline) buffer and elution in 0.2M Tris-glycine at pH 2.8, followed by neutralization to pH ~7.5.

Immunohistochemistry.

Adult mice under deep anesthesia were perfused with PBS and pancreata were quickly removed, incubated for 6 hours in 4% paraformaldehyde and processed for paraffin embedding. Sections of 8$\mu$m were used for immunocytochemistry. In brief, sections were incubated in the presence of 5% H2O2 for 30 min at room temperature, washed in PBS and incubated overnight in the presence of 5% bovine serum albumin dissolved in PBS buffer containing 0.5% Triton X-100 and 2% goat serum. The sections were then incubated for 14 hours at 4° C. with the affinity-purified preimmune or immune anti IB1 serum (dilution 1/200) and then for 2 hours at room temperature with the secondary antibody (biotinylated goat anti-rabbit IgG from Vector/Reactolab S.A.) and 2 hours at room temperature with avidin-biotinylated peroxidase complex (ABC, Vector Reactolab SA). The peroxidase reaction was finally visualized with 3,3'-diaminobenzidine tetrahydrochloride dihydrate (Fluka, Buchs, Switzerland) in PBS containing 0.2% H2O2. Photographs were taken with a Leica microscope using transmitted light optics and Kodak Ektachrome EPJ 320 films. For immunostaining the $\beta$TC3 or the transfected COS-7 cells, these cells were plated on glass coverslips 48 hours before the experiment. The cells were fixed in ice-cold methanol/acetone (50:50) and processed as described above with the ABC detection kit. In COS-7 cells, the detection of the FLAG epitope was obtained using as a secondary antibody, the commercially available (Kodak, New Haeven, Conn.) monoclonal mouse antibody directed against the FLAG subsequently visualized with fluoroscein isothiocyanate (FITC)-labelled goat anti-mouse antibodies. The rabbit anti-IB1 antibodies were detected using a Texas red-labelled goat anti-rabbit antibody. The fluorescence images were obtained with 1600 ASA Kodak films.

Results

Isolation and Sequence Analysis of the IB1 cDNA

The identification of a cis element named GTII located in the proximal region of the GLUT2 promoter which is functionally important to confer pancreatic expression of the gene was the initial step towards the identification of putative islet-specific trans-acting factors(3). Indeed, the GTII-binding activity was shown to be restricted to insulin-secreting cells and its abundance was highest in a cell line that expresses high amounts of endogenous GLUT2, the INS-1 cells (3). A poly-dT primed INS-1 cDNA expression libary was therefore constructed and screened by the procedure described by Singh et al (38) using as a probe concatanated GTII oligonucleotides. One positive clone was isolated from a primary screen of approximatively $2 \times 10^6$ phage plaques. The 2,990 bp long insert encodes a large open reading frame of 714 amino acids. The gene product contained in this clone was subsequently termed IB1 for Islet-Brain 1 as its expression is mainly restricted to these two tissues, as discussed below. The deduced amino acid sequence revealed the presence of a putative HLH dimerization domain conserved with other members of the bHLH family (SEQ ID NO:2) (FIG. 1). Using the SOPMA algorithm (self optimized prediction method from alignements, CNRS, Lyon, France), computer analysis predicts two acidic helicoidal structures (a.a. 31–61 and 114–125) and a proline-rich (a.a. 292–366) region in the amino-terminal part of the protein that could act as transactivation domains (25). Putative nuclear localisation signals were also recognized (a.a. 163–190 and 242–270) (8).

Tissue Distribution of IB1 Expression.

Northern blot analysis of total RNA and polyA$^+$ RNA from several adult rat tissues and cell lines indicated that IB1 is abundantly expressed as a 3 and 3.2 kb transcript in several insulin-secreting cell lines (INS-1 and RIN5F), in isolated pancreatic islets and in the brain (FIG. 2). IB1 transcripts were also detected, although to a lower extent, in the kidney and the heart. In this latter, a single 3.2 kb transcript was detected. In the brain, IB1 expression is highest in the cortex and in the pituitary gland, although the IB1 transcripts were also detected in the hypothalamus, the cerebellum and the medulla (FIG. 2D). In the isolated pancreatic islets, IB1 expression was not regulated by increasing the glucose concentration in the incubation medium from 2.8 mM to 30 mM suggesting that the gene is not transcriptionnaly regulated by glucose as this is the case for GLUT2 (52). IB1 expression is therefore restricted to a few tissues and, importantly, the IB1 mRNA is not detected in the liver where GLUT2 is abundantly expressed.

IB7 is Immunodetected in Rat Tissues and in Insulin-secreting Cell Lines.

Antibodies were raised against the bacterially-produced N-terminal part of IB1(a.a. 1–280). These polyclonal antibodies were affinity purified as described in Materials and Methods and used in Western blotting. As shown in FIG. 3A, these antibodies detect a 120 kDa protein in $\beta$TC3 nuclear exctracts which comigrate with the product obtained by in vitro translating the IB1 cDNA in presence of $^{35}$S methionine (FIG. 3B). Similarly, the IB1 protein could be detected in both the nuclear and cytoplasmic extracts obtained from COS-7 cells transiently transfected with the CMV driven IB1 cDNA, which suggests that IB1is actively translocated in the nucleus (FIG. 3C and D) . A survey of several rat tissues confirmed that the IB1transcripts expressed in brain are translated into immunodetectable protein once analyzed by Western blotting (FIG. 3E).

To gain further information regarding the tissue and cellular localization of IB1 within the pancreas, immunohistochemistry studies were performed on mouse islets and βTC3 cells. Using the affinity-purified antibodies directed against IB1, this factor was detected in the pancreatic islet (FIG. 4A), with a staining which differs from the one obtained with the anti-GLUT2 (FIG. 4B) or the anti-insulin (FIG. 4C) antibodies. The immunostaining reaction is negative in βTC3 cells incubated with preimmune serum (FIG. 4D) whereas the signal was expositive in the nuclei and the cytoplasm of the same cells exposed to the anti-IB1serum (FIG. 4E and F). In order to confirm the specificity of the anti-IB1 antibodies in immunocytochemistry, a construct was generated which includes a FLAG epitope N-terminal to the IB1 protein expressed under the control of a CMV promoter. This construct was transiently transfected into COS-7 cells, immunodetected with an anti-FLAG antibody subsequently visualized by FITC-staining (FIG. 4H) or with the anti-IB1antibody subsequently visualized with an anti-rabbit Texas red-labeled antibody (FIG. 4I). The IB1protein was detected in transfected COS-7 cells with both the anti-FLAG and the anti-IB1 antibodies confirming that the protein is, at least in part, correctly translocated to the nuclei of COS-7 cells and that the anti-IB1 antibody is specific to IB1.

The IB7 Protein Binds Specifically to GTII and to the Insulin Enhancer Sequence RIPE3.

By analogy with PDX-1 which was shown to be an homeodomain transcription factor and which is expressed specifically in the pancreatic islets and is able to control several genes expressed only in these cells through homologous DNA sequences (22,24,28,53,54), we hypothesized that IB1 could similarly control several genes within the β-cells. The GTII cis sequence used for the expression cloning of IB1 shares some nucleic acid sequences identity with an important enhancer sequence of the insulin promoter termed RIPE3 for rat insulin promoter element 3. This RIPE3 element was previously shown to participate in the β-cell specific control of the insulin gene (17,20). As depicted in FIG. 5A, some conserved nucleic acid sequences are present between GTII and RIPE3.

By SouthWestern analysis of INS-1 nuclear extracts, both the GTII and RIPE3 probes detected a 120 kDa protein which is similar in size to the product obtained by in vitro translating the IB1 cDNA in presence of $^{35}S$ methionine and to the protein detected using anti-IB1 antibodies (FIG. 5B). Furthermore, the IB1 cDNA was cloned 3' to a CMV promoter and transiently transfected into COS-7, a cell line lacking endogenous IB1. Crude cellular extracts were subsequently analyzed by the SouthWestern technique using the GTII probe. Only IB1 -transfected COS-7 cells express the expected 120 kDa GTII-binding protein (FIG. 5C) The IB1cDNA is therefore translated into an 120 kDa product which is able to bind the GTII probe in a manner similar to the endogenous binding activity observed in INS-1 or βTC3 nuclear extracts.

Gel retardation analysis were also conducted using either the GTII or the RIPE3 elements as probe with βTC3 nuclear extracts. A shown in FIG. 5D, the GTII-binding activity is competed with an excess of cold RIPE3 and inversely, the RIPE3 binding activity is competed with an excess of cold GTII nucleotides. Therefore, similar DNA-binding activities present in insulin secreting cells interact with both the GTII and the RIPE3 regulatory sequences. This suggests that IB1, which binds GTII and RIPE3, may regulates expression of the GLUT2 and insulin genes.

Transcriptional Activation by IB1

Transcriptional activation by IB1 was assayed by cotransfection experiments in the insulin-secreting cell line βTC3 and in a glucagon producing cell line (InR1-G9) as well as the non pancreatic-derived cell line COS-7 cells with an IB1 expression vector (PBK/IB1) and several reporter contructs (FIG. 6A). The wild-type insulin I promoter region (−410 bp) and the proximal region of the GLUT2 promoter (−338 bp) were linked to a luciferase reporter gene and transiently transfected in these cell lines. Overexpression of IB1 transactivated the GLUT2 promoter 1.7 fold whereas the insulin gene was induced 3.8 fold when compared to a co-transfection with the expression vector lacking the IB1 cDNA (PBKS). This effect was restricted to the insulin-secreting cells and clearly absent with the promoterless reporter construct (pGL3). The restricted action of IB1 in β-cells suggest that IB1 functions only in the presence of other regulators present in pancreatic β-cells, possibly others yet-to-be-identified β-cell specific transcription factors. Several 5' deletion constructs of the rat insulin I promoter were then similarly transfected into βTC3 cells in the presence or the absence of the expression vector encoding IB1. This latter transactivated several exonuclease III-deleted regions of the insulin promoter, although this effect was lower once constructs 3' to the −159 bp were used (FIG. 6B). This indicates that the RIPE3 sequence located 5' to the −159 bp of the promoter could be an important regulatory element through which IB1 transactivates the insulin gene (13). For the next series of experiments we adressed the question whether IB1 could mediate its stimulatory effect through the RIPE3 enhancer sequence of the rat insulin II gene. This enhancer sequence has been extensively studied by several investigators. Two separate subelements of RIPE3, RIPE3a and RIPE3b, function cooperatively to generate maximal activity of this tissue-specific enhancer (17). Each subelement binds ubiquitously expressed or β-cell specific trans-acting factors such as BETA1, BETA2 and E47 (26,27,34, 37). Most interestingly, the BETA2/E47 heterodimer has been shown to be a potent transactivator of the RIPE3 elements, effect mediated through the E box located within the RIPE3a subelement (27). However, this stimulatory effect necessitate the RIPE3b adjacent subelement where putative β-cell specific trans-acting factor(s) may bind to optimalize the stimulatory effect the HLH factors. To investigate if IB1 is one of the possible partners of the RIPE3 binding factors, 5 copies of the RIPE3 element were cloned 5' to a minimal heterologous promoter (SV40) linked to a luciferase gene. This construct or its parent vector (SV40 luciferase) were transfected into βTC3 cells with or without the expression vector encoding IB1. As shown in FIG. 6C, IB1 transactivated the RIPE3 construct 5 fold and this effect was not present in the glucagon producing cell line InR1-G9 (data not shown). Taken together, these results confirm that IB1 is a component of the RIPE3 binding factors as evaluated by Southwestern analyses and cross-competition assays with the RIPE3 and GTII elements (FIG. 5) and as evaluated by the functional data obtained with the RIPE3 construct (FIG. 6).

Discussion

The above results show the isolation and characterization of a new transactivator of the GLUT2 and the insulin genes. This factor, termed IB1, is highly expressed in pancreatic β-cells and was isolated by its ability to bind to a cis regulatory element of the GLUT2 promoter. We also demonstrate that IB1 is able to bind to a homologous regulatory element of the insulin gene, RIPE3. This enhancer sequence contains two separate sub-elements, RIPE3a and RIPE3b, which function cooperatively to generate maximal activity of this tissue-specific enhancer (Hwung et al., 1990). RIPE3 binds ubiquitously expressed and β-cell specific trans-acting factors such as BETA1, BETA2 and E47 (Shieh and Tsai, 1991; Murre et al., 1989; Peyton et al., 1994; Naya et al., 1995). The BETA2/E47 heterodimer has been shown to be a potent transactivator of the RIPE3 element, an effect mediated through the E box located within the RIPE3a subelement (Naya et al., 1995). This stimulatory effect necessitates the RIPE3b adjacent sub-element where yet-to-be-identified β-cell specific trans-acting factor(s) bind. As IB1 is able to bind RIPE3 in vitro and as this factor is able to transactivate RIPE3 mediated reporter gene expression in β cells, we propose that IB1 is one of the important partners of the RIPE3-binding proteins. The competition assays using as probe either GTII or RIPE3 demonstrated that the GTII-binding proteins have a high affinity for the GTII cis element, however they are competed with an excess of cold RIPE3 oligonucleotides. Conversely, the RIPE3-binding proteins detected by mobility shift (EMSA) assay with the RIPE3 probe are competed with an excess of cold GTII. However, we were unable to supershift, using anti-IB1 antibodies, the GTII- or RIPE3-binding activities detected by EMSA. This observation suggests that the antibodies raised against IB1 are unable to detect IB1 in non-denaturating conditions where the epitopes may be masked by other binding proteins. Furthermore, IB1 binding activity necessitates post-translational modifications. Dephosphorylation of βTC3 nuclear extracts abolishes the binding of IB1 to GTII or RIPE3 when assessed by SouthWestern analysis (our unpublished data). Functionally, IB1 is a transactivator of the GLUT2 promoter (170% increase over basal) but a potent inducer of insulin gene transcription (380% increase over basal). This effect may reflect the higher binding affinity of IB1 to GTII rather than RIPE3 (see FIG. 5). As IB1 functions only in β-cell lines where endogenous IB1 is present, one may speculate that the GLUT2 reporter construct cannot be stimulated with the expression vector encoding IB1 since the high affinity GTII cis elements are already occupied by endogenous IB1. More recently, Stellrecht and co-authors have elegantly demonstrated that multiple copies of the RIPE3 sequence are able to drive reporter gene expression in a restricted manner in pancreatic β-cells and in the brain of transgenic mice (Stellrecht et al., 1997). As IB1 expression is the highest in the brain and in β-cells and as this factor transactivates the insulin gene through RIPE3, these observations show that IB1 participates in the tissue-specific control of the insulin gene.

As observed with BETA2, IB1 is expressed in a highly restricted manner (Naya et al., 1995). BETA2 is found in α-and β-cells and in the brain whereas IB1 expression is present only in β-cells, in the brain and to a lower extent in the heart and the kidney. Interestingly, GLUT2 is expressed in β-cells, in the gut, the kidney, the liver and in a subset of neurons (Thorens et al., 1988; Leloup et al., 1994; Orci et al., 1989) and the gene encoding GLUT2 is abnormally regulated only in the endocrine pancreas when diabetes is present (Johnson et al., 1990; Ohneda et al., 1993; Orci et al., 1990b; Orci et al., 1990a; Thorens et al., 1992; Thorens et al., 1990; Unger, 1991). As IB1 is a transactivator of the insulin and the GLUT2 genes and as IB1 expression is mainly restricted to β-cells and is not expressed in liver, abnormal expression or function of IB1 could be responsible for the diabetic- and β-cell specific dysregulation of GLUT2. Phosphorylation is necessary, as a post translational modification of IB1, to allow the binding of IB1 to its recognition site. Some β-cell functions, including phosphorylating activities, are altered during diabetes and therefore could induce a loss of IB1 binding activity.

The recent identification of mutations present in the transcription factors HNF-1a and HNF-4α, factors which are weak transactivators of the insulin gene and which are also expressed in β-cells, is of interest since they are responsible for the onset of two forms of diabetes, MODY3 and MODY1, respectively (Yamagata et al., 1996b; Yamagata et al., 1996a).

An intriguing observation on IB1is its subcellular localization as it is located in both the cytoplasmic and nuclear compartments. IB1 contains a putative nuclear translocation signal (Dingwall and Laskey, 1991) and several lines of evidence suggest that indeed, IB1 is a nuclear protein. First, IB1 is a DNA-binding protein as this factor has been cloned based on its ability to bind to the GTII cis element. Second, the SouthWestern experiments could detect IB1 in nuclear extracts of transfected COS cells with the expression vector encoding IB1. Third, immunodetectable nuclear staining is present by histochemistry in pancreatic islets as well as in βTC3 cells and Western blot analysis of these cells could also detect IB1 in the cytoplasm and the nucleus. Finally, IB1 is clearly a transactivator of the GLUT2 and the insulin promoter linked to a reporter gene which implies that this factor functions as a transcription factor. The mechanisms responsible for the active translocation of IB1 in the nucleus are not yet understood but could be of importance as IB1 transacting functions may simply depend on the control of translocation. Several other similar observations are described where a DNA binding protein is sequestrated in the cytoplasm and translocated into the nucleus once proper stimulus is present. NFκKB is sequestered in the cytoplasm by an interaction with Iκ-B (Beg et al., 1992). Once phosphorylated, the complex is dissociated and NFκB is translocated in the nucleus and acts as a transactivator (Ghosh and Baltimore, 1990). BZP has also recently been described as a zinc finger DNA-binding protein expressed in β-cells (Franklin et al., 1994). Serum deprivation caused BZP to remain cytoplasmic, whereas the adjunction of serum induces BZP translocation allowing its function as an inhibitor of gene transcription. The mechanism of sequestration of the cAMP responsive element binding protein (CREB) in the cytoplasm of germinal cells has also been described and involves the formation of a truncated CREB protein, lacking the nuclear translocation signal, by the use of an alternatively spliced exon (Waeber and Habener, 1991; Waeber et al., 1991). The mechanisms which trigger the translocation of IB1 into the nucleus might involve glucose, serum or any cellular component such as cAMP or ATP. This issue is important to resolve as the IB1 transactivating function may be dependent upon proper regulated translocation of the protein into the nucleus.

Taken together, the above results demonstrate that IB1 is a novel DNA-binding protein which is expressed in a highly restricted manner in β-cells and in the brain, which functions, together with other unidentified β-cell specific factors, as a transactivator of the GLUT2 and the insulin gene through homologous DNA sequences. Due to the restricted expression of IB1, we propose that IB1 is an important factor which confers β-cell-specificity to the insulin and GLUT2 genes.

References:
1. Asfari, M., Janjic, D., Meda, P., Li, G., Halban, P. A. and Wollheim, C. B. Establishment of 2-mercaptoethanol-dependent differentiated insulin-secreting cell lines. *Endocrinology* 130:167–178, 1992.
2. Beg, A. A., Ruben, S. M., Scheinman, R. I., Haskill, S., Rosen, C. A. and Baldwin, A. S. IkB interacts with the nuclear localization sequences of the subunits of NF–kB: a mechanism for cytoplamic retention. *Genes and Development* 6:1899–1913, 1992.

3. Bonny, C., Thompson, N., Nicod, P. and Waeber, G. Pancreatic-specific expression of the glucose transporter type 2 gene: identification of cis-elements and islet-specific trans-acting factors. *Mol Endo* 9:1413–1426, 1995.

4. Brasier, A. R., Tate, J. E. and Habener, J. F. Optimized use of the firefly luciferase assay as a reporter gene in mammalian cell lines. *Biotechniques* 7:1116–1121, 1989.

5. De Vos, A., Heimberg, H., Quartier, E., et al. Human and rat beta cells differ in glucose transporter but not in glucokinase gene expression. *J Clin Invest* 96:2489–2495, 1995.

6. Deltour, L., Leduque, P., Blume, N., et al. Differential expression of two nonallelic proinsulin genes in the developing mouse embryo *Proc Natl Acad Sci USA* 90:527–531, 1993.

7. Dent, C. L. and Latchman, D. S. *Transcription Factors: A Practical Approach*, New York:Oxford University Press, 1993. pp. 1–26.

8. Dingwall, C. and Laskey, R. A. Nuclear targeting sequences-a consensus? *TIBS* 16:478–481, 1991.

9. Efrat, S., Linde, S., Kofod, H., et al. Beta-cell lines derived from transgenic mice expressing a hybrid insulin gene-oncogene. *Proc. Natl. Acad. Sci. USA* 85:9037–9041, 1988.

10. Ferber, S., Beltrandelrio, H., Johnson, J. H., et al. GLUT-2 gene transfert into insulinoma cells confers both low and high affinity glucose-stimulated insulin release. *J. Biol. Chem.* 269:11523–11529, 1994.

11. Ferrer, J., Benito, C. and Gomis, R. Pancreatic islet GLUT2 glucose transporter mRNA and protein expression in humans with and without NIDDM. *Diabetes* 44:1369–1374, 1995.

12. Franklin, A. J., Jetton, T. S., Shelton, K. D. and Magnuson, M. A. BZP, a novel serum-responsive zinc finger protein that inhibits gene transcription. *Mol and Cell Biology* 14:6773–6788, 1994.

13. German, M., Ashcroft, S., Docherty, K., et al. The insulin gene promoter. A simplified nomemclature. *Diabetes* 44:1002–1004, 1995.

14. Ghosh, S. and Baltimore, D. Acivation in vitro of NF–kB by phosphorylation of its inhibitor IkB. *Nature* 344:678–682, 1990.

15. Gotoh, M., Maki, T., Satomi, T., et al. Reproducible high yield of rat islets by stationary in vitro digestion following pancreatic ductal or portal venous collagenase injection. *Transplantation* 43:725–730, 1987.

16. Hughes, S. D., Quaade, C., Johnson, J. H., Ferber, S. and Newgard, C. B. Transfection of AaT-20ins cells with GLUT2 but not GLUT1 confers glucose-stimulated insulin secretion. Relationship to glucose metabolism. *J. Biol. Chem.* 268:15205–15212, 1993.

17. Hwung, Y. -P., Gu, Y. -Z. and Tsai, M. -J. Cooperativity of sequence elements mediates tissue specificity of the rat insulin II gene. *Mol and Cell Biology* 10:1784–1788, 1990.

18. Johnson, J. H., Ogawa, A., Chen, L., et al. Underexpression of B-cell high Km glucose transporters in noninsulin-dependent diabetes. *Science* 250:546–548, 1990.

19. Jonsson, J., Carlsson, L., Edlund, T. and Edlund, E. Insulin-promoter-factor 1 is required for pancreas development in mice. *Nature* 371:606–609, 1994.

20. Karlsson, O., Edlund, J. B., Moss, J. B., Rutter, W. J. and Walker, M. D. A mutational anlysis of the insulin gene transcription control region: expression in beta cells is dependent on two related sequences within the enhancer. *Proc Natl Acad Sci USA* 84:8819–8823, 1987.

21. Leloup, C., Arluison, M., Lepetit, N., et al. Glucose transporter 2(GLUT2): expression in specific brain nuclei. *Brain Research* 638:221–226, 1994.

22. Leonard, J., Peers, B., Johnson, T., Ferreri, K., Lee, S. and Montminy, M. R. Characterization of somatostatin transactivating factor-1, a novel homeobox factor that stimulates somatostatin expression in pancreatic islet cells. *Mol Endo* 7:1275–1283, 1993.

23. McKnight, S. L. and Kingsbury, R. Transcription control signals of eukaryotic protein coding gene. *Science* 217:316–324, 1982.

24. Miller, C. P., McGehee, R. E., Jr and Habener, J. F. IDX-1: a new homeodomain transcription factor expressed in rat pancreatic islets and duodenum that transactivates the somatostatin gene. *EMBO J* 13:1145–1156, 1994.

25. Mitchell, P. J. and Tjian, R. Transcriptional regulation in mammalian cells by sequence-specific DNA binding proteins. *Science* 245:371–378, 1989.

26. Murre, C., McCaw, P. S., Vaessin, H., et al. Interactions between heterologous helix-loop-helix proteins generate complexes that bind specifically to a common DNA sequence. *Cell* 58:537–544, 1989.

27. Naya, F. J., Stellrecht, C. M. M. and Tsai, M. -J. Tissue-specific regulation of the insulin gene by a novel helix-loop-helix transcription factor. *Genes and Development* 9:1009–1019, 1995.

28. Ohlsson, H., Karlsson, K. and Edlund, T. IPF1, a homeodomain-containing transactivator of the insulin gene. *EMBO J* 12:4251–4259, 1993.

29. Ohneda, M., Johnson, J. H., Inman, L. R., et al. GLUT2 expression and function in b-cells of GK rats with NIDDM. *Diabetes* 42:1065–1072, 1993.

30. Orci, L., Ravazzola, M., Baetens, D., et al. Evidence that down-regulation of B-cell glucose transporters in non-insulin-dependent diabetes may be the cause of diabetic hyperglycemia. *Proc. Natl. Acad. Sci. USA* 87:9953–9957, 1990.

31. Orci, L., Thorens, B., Ravazzola, M. and Lodish, H. F. Localization of the pancreatic b-cell glucose transporter to specific plasma membrane domains. *Science* 245:295–297, 1989.

32. Orci, L., Unger, R. H., Ravazzola, M., et al. Reduced B-cell glucose transporter in new onset diabetic BB rats. *J Clin Invest* 86:1615–1622, 1990.

33. Pearse, A. G. E. and Polak, J. Neural crest origin of the endocrine polypeptide (APUD) cells of the gastrointestinal tract and pancreas. *gut* 12:783–788, 1971.

34. Peyton, M., Moss, L. and Tsai, M. -J. Two distinct class A helix-loop-helix transcription factors, E2A and BETA1, form separate DNA binding complexes on the insulin gene E-box. *J Biol Chem* 269:25936–25941, 1994.

35. Rencurel, F., Waeber, G., Antoine, B., Rocchiccioli, F., Maulard, P. and Girard, J. Requirement of glucose metabolism for regulation of glucose transporter type 2 (GLUT2) gene expression in liver. *Biochem J* 314:903–909, 1996.

36. Rencurel, F., Waeber, G., Bonny, C., et al. Cyclic adenosine monophosphate prevents the glucose-mediated stimulation of GLUT2 gene transcription in hepatocytes. *Biochem J* 322:441–448, 1997.

37. Shieh, S. Y. and Tsai, M. -J. Cell-specific and ubiquitous factors are responsible for the enahncer activity of the rat insulin II gene. *J. Biol. Chem.* 266:16707–16714, 1991.

38. Singh, H., LeBowitz, J. H., Baldwin, A. S. and Sharp, P. A. Molecular cloning of an enhancer binding protein: isolation by screening of an expression library with a recognition site DNA. *Cell* 52:415–423, 1988.

39. Stoffers, D., Zinkin, N. T., Stanojevic, V., Clarke, W. L. and Habener, J. F. Pancreatic agenesis attributable to a single nucleotide deletion in the human IPF1 gene coding sequence. *Nature Genetics* 15:106–110, 1997.
40. Takaki, R., Ono, J., Nakamura, M., et al. Isolation of glucagon-secreting cell lines by cloning insulinoma cells in vitro. In Vitro *Cell Dev. Biol.* 22:120–126, 1986.
41. Teitelman, G., Alpert, S., Polak, J. M., Martinez, A. and Hanahan, D. Precursor cells of mouse endocrine pancreas coexpress insulin, glucagon and the neuronal proteins tyrosine hydroxylase and neuropeptide Y, but not pancreatic polypeptide. *Development* 118:1031–1039, 1993.
42. Teitelman, G. and Lee, J. K. Cell lineage analysis of pancreatic islet cell development:glucagon and insulin cells arise from catecholaminergic precursors present in the pancreatic duct. *Dev. Biol.* 121:454–466, 1987.
43. Thorens, B. Molecular and cellular physiology of GLUT2, a high Km facilitated diffusion glucose transporter. *Int. Review of Cytology* 137A:209–237, 1992.
44. Thorens, B., Sarkar, H. K., Kaback, H. R. and Lodish, H. F. Cloning and functional expression in bacteria of a novel glucose transporter present in liver, intestine, kidney, and b-pancreatic islet cells. *Cell* 55:281–290, 1988.
45. Thorens, B., Weir, G. C., Leahy, J. L., Lodish, H. F. and Bonner-Weir, S. Reduced expression of the liver/beta-cell glucose transporter isoform in glucose-insensitive pancreatic beta cells of diabetic rats. *Proc. Natl. Acad. Sci. USA* 87:6492–6496, 1990.
46. Thorens, B., Wu, Y. -J., Leahy, J. L. and Weir, G. C. The loss of GLUT2 expression by glucose-unresponsive B cells of db/db mice is reversible and is induced by the diabetic environment. *J Clin Invest* 90:77–85, 1992.
47. Unger, R. H. Diabetic hyperglycemia-link to impaired high Km glucose transport in pancreatic b-cells. *Science* 251:1200–1205, 1991.
48. Valera, A., Solanes, G., Fernandez-Alvarez, J., et al. Expression of Glut-2 antisense RNA in b cells of transgenic mice leads to diabetes. *J. Biol. Chem.* 269:28543–28546, 1994.
49. Waeber, G. and Habener, J. F. Nuclear translocation and DNA recognition signals co-localized within the bZIP domain of cyclic AMP response element binding protein CREB. *Mol Endo* 10:1431–1438, 1991.
50. Waeber, G., Meyer, T. E., Lesieur, M., hermann, H. L., Gerard, N. and Habener, J. F. Developmental stage-specific expression of the cyclic AMP response element binding protein CREB during spermatogenesis involves alternative exon splicing. *Mol Endo* 10:1419–1430, 1991.
51. Waeber, G., Pedrazzini, T., Bonny, O., et al. A 338 bp proximal fragment of the glucose transporter type 2 (GLUT2) promoter drives reporter gene expression in the pancreatic islets of transgenic mice. *Mol Cell Endocrinol* 114:205–215, 1995.
52. Waeber, G., Thompson, N., Haefliger, J. -A. and Nicod, P. Characterization of the murine high Km glucose transporter GLUT2 gene and its transcriptional regulation by glucose in a differentiated insulin-secreting cell line. *J Biol Chem* 269:26912–26919, 1994.
53. Waeber, G., Thompson, N., Nicod, P. and Bonny, C. Transcriptional activation of the GLUT2 gene by the IPF-1/STF-1/IDX-1 homeobox factor. *Mol Endo* 10:1327–1334, 1996.
54. Watada, H., Kajimoto, Y., Umayahara, Y., et al. The human glucokinase gene beta-cell promoter: an essential role of insulin promoter factor 1/PDX-1 in its activation in HIT-T15 cells. *Diabetes* 45:1478–1488, 1996.
55. Yamagata, K., Furuta, H., Oda, N., et al. Mutations in the hepatocyte nuclear factor-4a in maturity-onset diabetes of the young (MODY1). *Nature* 384:458–460, 1996.
56. Yamagata, K., Oda, N., Kaisaki, P. J., et al. Mutations in the heaptocyte nuclear factor-1a gene in maturity-onset diabetes of the young (MODY3). *Nature* 384:455–458, 1996.

What is claimed is:

1. An isolated IB1 polypeptide comprising a polypeptide having the amino acid sequence set out as SEQ ID NO:2.

2. An isolated IB1 polypeptide comprising a polypeptide having the amino acid sequence set out as SEQ ID NO:4.

3. A composition comprising an IB1 polypeptide having the amino acid sequence set out as SEQ ID NO:2 and a carrier.

4. A composition comprising an IB1 polypeptide having the amino acid sequence set out as SEQ ID NO:4 and a carrier.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 2953 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 108..2252

( x i ) SEQUENCE DESCRIPTION: SEQ ID NO:1:

```
CCGCCCCAGC   TCAGTCCGAA   CCCCGCGGCG   GCGGCGGCCT   CCTCCACACG   CCTCCACCTC              60

CGCCGCCGCC   GCCGCCGCCG   CCGCCTCCCG   CGCCGCTCTC   CGCCCGG ATG   GCC   AGG             116
                                                           Met   Ala   Arg
                                                            1

CTG   AGC   CCG   GGA   ATG   GCG   GAG   CGA   GAG   AGC   GGC   CTG   AGC   GGG   GGT   GCC    164
Leu   Ser   Pro   Gly   Met   Ala   Glu   Arg   Glu   Ser   Gly   Leu   Ser   Gly   Gly   Ala
      5                       10                        15

GCG   TCC   CCA   CCG   GCC   GCT   TCC   CCA   TTC   CTG   GGA   CTG   CAC   ATC   GCG   TCG    212
```

| | | | | | | | | | | | | | | | |
|---|---|---|---|---|---|---|---|---|---|---|---|---|---|---|---|
| Ala | Ser | Pro | Pro | Ala | Ala | Ser | Pro | Phe | Leu | Gly | Leu | His | Ile | Ala | Ser |
| 20 | | | | 25 | | | | | 30 | | | | | | 35 |

| CCT | CCC | AAT | TTC | AGG | CTC | ACC | CAT | GAT | ATC | AGC | CTG | GAG | GAG | TTT | GAG | 260 |
|---|---|---|---|---|---|---|---|---|---|---|---|---|---|---|---|---|
| Pro | Pro | Asn | Phe | Arg | Leu | Thr | His | Asp | Ile | Ser | Leu | Glu | Glu | Phe | Glu | |
| | | | | 40 | | | | | 45 | | | | | 50 | | |

| GAT | GAA | GAC | CTT | TCG | GAG | ATC | ACT | GAT | GAG | TGT | GGC | ATC | AGC | CTG | CAG | 308 |
|---|---|---|---|---|---|---|---|---|---|---|---|---|---|---|---|---|
| Asp | Glu | Asp | Leu | Ser | Glu | Ile | Thr | Asp | Glu | Cys | Gly | Ile | Ser | Leu | Gln | |
| | | | | 55 | | | | | 60 | | | | | 65 | | |

| TGC | AAA | GAC | ACC | TTG | TCT | CTC | CGG | CCC | CCG | CGC | GCC | GGG | CTA | CTG | TCT | 356 |
|---|---|---|---|---|---|---|---|---|---|---|---|---|---|---|---|---|
| Cys | Lys | Asp | Thr | Leu | Ser | Leu | Arg | Pro | Pro | Arg | Ala | Gly | Leu | Leu | Ser | |
| | | 70 | | | | | 75 | | | | | 80 | | | | |

| GCG | GGT | AGC | AGC | GGT | AGC | GCG | GGG | AGC | CGG | CTG | CAG | GCG | GAG | ATG | CTG | 404 |
|---|---|---|---|---|---|---|---|---|---|---|---|---|---|---|---|---|
| Ala | Gly | Ser | Ser | Gly | Ser | Ala | Gly | Ser | Arg | Leu | Gln | Ala | Glu | Met | Leu | |
| | | 85 | | | | 90 | | | | | 95 | | | | | |

| CAG | ATG | GAC | CTG | ATC | GAC | GCG | GCA | AGT | GAC | ACT | CCG | GGC | GCC | GAG | GAC | 452 |
|---|---|---|---|---|---|---|---|---|---|---|---|---|---|---|---|---|
| Gln | Met | Asp | Leu | Ile | Asp | Ala | Ala | Ser | Asp | Thr | Pro | Gly | Ala | Glu | Asp | |
| 100 | | | | | 105 | | | | | 110 | | | | | 115 | |

| GAC | GAA | GAG | GAC | GAC | GAC | GAG | CTC | GCT | GCC | CAA | CGG | CCA | GGA | GTG | GGG | 500 |
|---|---|---|---|---|---|---|---|---|---|---|---|---|---|---|---|---|
| Asp | Glu | Glu | Asp | Asp | Asp | Glu | Leu | Ala | Ala | Gln | Arg | Pro | Gly | Val | Gly | |
| | | | | 120 | | | | | 125 | | | | | 130 | | |

| CCT | TCC | AAA | GCC | GAG | TCT | GGC | CAG | GAG | CCG | GCG | TCT | CGC | AGC | CAG | GGT | 548 |
|---|---|---|---|---|---|---|---|---|---|---|---|---|---|---|---|---|
| Pro | Ser | Lys | Ala | Glu | Ser | Gly | Gln | Glu | Pro | Ala | Ser | Arg | Ser | Gln | Gly | |
| | | | 135 | | | | | 140 | | | | | 145 | | | |

| CAG | GGC | CAG | GGC | CCC | GGC | ACA | GGC | TGC | GGA | GAC | ACC | TAC | CGG | CCC | AAG | 596 |
|---|---|---|---|---|---|---|---|---|---|---|---|---|---|---|---|---|
| Gln | Gly | Gln | Gly | Pro | Gly | Thr | Gly | Cys | Gly | Asp | Thr | Tyr | Arg | Pro | Lys | |
| | | 150 | | | | | 155 | | | | | 160 | | | | |

| AGG | CCT | ACC | ACG | CTC | AAC | CTT | TTC | CCG | CAG | GTG | CCG | CGG | TCT | CAG | GAC | 644 |
|---|---|---|---|---|---|---|---|---|---|---|---|---|---|---|---|---|
| Arg | Pro | Thr | Thr | Leu | Asn | Leu | Phe | Pro | Gln | Val | Pro | Arg | Ser | Gln | Asp | |
| | 165 | | | | | 170 | | | | | 175 | | | | | |

| ACG | CTG | AAT | AAT | AAC | TCT | TTA | GGC | AAA | AAG | CAC | AGT | TGG | CAG | GAC | CGT | 692 |
|---|---|---|---|---|---|---|---|---|---|---|---|---|---|---|---|---|
| Thr | Leu | Asn | Asn | Asn | Ser | Leu | Gly | Lys | Lys | His | Ser | Trp | Gln | Asp | Arg | |
| 180 | | | | | 185 | | | | | 190 | | | | | 195 | |

| GTG | TCT | CGA | TCA | TCC | TCC | CCT | CTG | AAG | ACA | GGG | GAG | CAG | ACG | CCT | CCA | 740 |
|---|---|---|---|---|---|---|---|---|---|---|---|---|---|---|---|---|
| Val | Ser | Arg | Ser | Ser | Ser | Pro | Leu | Lys | Thr | Gly | Glu | Gln | Thr | Pro | Pro | |
| | | | | 200 | | | | | 205 | | | | | 210 | | |

| CAT | GAA | CAT | ATC | TGC | CTG | AGT | GAT | GAG | CTG | CCG | CCC | CAG | GGC | AGT | CCT | 788 |
|---|---|---|---|---|---|---|---|---|---|---|---|---|---|---|---|---|
| His | Glu | His | Ile | Cys | Leu | Ser | Asp | Glu | Leu | Pro | Pro | Gln | Gly | Ser | Pro | |
| | | | 215 | | | | | 220 | | | | | 225 | | | |

| GTT | CCC | ACC | CAG | GAT | CGT | GGC | ACT | TCC | ACC | GAC | AGC | CCT | TGT | CGC | CGT | 836 |
|---|---|---|---|---|---|---|---|---|---|---|---|---|---|---|---|---|
| Val | Pro | Thr | Gln | Asp | Arg | Gly | Thr | Ser | Thr | Asp | Ser | Pro | Cys | Arg | Arg | |
| | | 230 | | | | | 235 | | | | | 240 | | | | |

| ACT | GCA | GCC | ACC | CAG | ATG | GCA | CCT | CCA | AGT | GGT | CCC | CCT | GCC | ACT | GCA | 884 |
|---|---|---|---|---|---|---|---|---|---|---|---|---|---|---|---|---|
| Thr | Ala | Ala | Thr | Gln | Met | Ala | Pro | Pro | Ser | Gly | Pro | Pro | Ala | Thr | Ala | |
| | 245 | | | | | 250 | | | | | 255 | | | | | |

| CCT | GGT | GGC | CGG | GGC | CAC | TCC | CAT | CGA | GAT | CGG | TCC | ATA | TCA | GCA | GAT | 932 |
|---|---|---|---|---|---|---|---|---|---|---|---|---|---|---|---|---|
| Pro | Gly | Gly | Arg | Gly | His | Ser | His | Arg | Asp | Arg | Ser | Ile | Ser | Ala | Asp | |
| 260 | | | | | 265 | | | | | 270 | | | | | 275 | |

| GTG | CGG | CTC | GAG | GCG | ACT | GAG | GAG | ATC | TAC | CTG | ACC | CCA | GTG | CAG | AGG | 980 |
|---|---|---|---|---|---|---|---|---|---|---|---|---|---|---|---|---|
| Val | Arg | Leu | Glu | Ala | Thr | Glu | Glu | Ile | Tyr | Leu | Thr | Pro | Val | Gln | Arg | |
| | | | | 280 | | | | | 285 | | | | | 290 | | |

| CCC | CCA | GAC | CCT | GCA | GAA | CCC | ACC | TCC | ACC | TTC | TTG | CCA | CCC | ACT | GAG | 1028 |
|---|---|---|---|---|---|---|---|---|---|---|---|---|---|---|---|---|
| Pro | Pro | Asp | Pro | Ala | Glu | Pro | Thr | Ser | Thr | Phe | Leu | Pro | Pro | Thr | Glu | |
| | | | 295 | | | | | 300 | | | | | 305 | | | |

| AGC | CGG | ATG | TCT | GTC | AGC | TCG | GAT | CCT | GAC | CCT | GCC | GCT | TAC | TCT | GTA | 1076 |
|---|---|---|---|---|---|---|---|---|---|---|---|---|---|---|---|---|
| Ser | Arg | Met | Ser | Val | Ser | Ser | Asp | Pro | Asp | Pro | Ala | Ala | Tyr | Ser | Val | |
| | | 310 | | | | | 315 | | | | | 320 | | | | |

| ACT | GCA | GGG | CGA | CCG | CAC | CCT | TCC | ATC | AGT | GAA | GAG | GAT | GAG | GGC | TTC | 1124 |
|---|---|---|---|---|---|---|---|---|---|---|---|---|---|---|---|---|
| Thr | Ala | Gly | Arg | Pro | His | Pro | Ser | Ile | Ser | Glu | Glu | Asp | Glu | Gly | Phe | |
| | 325 | | | | | 330 | | | | | 335 | | | | | |

| GAC | TGT | CTG | TCA | TCC | CCA | GAG | CAA | GCT | GAG | CCA | CCA | GGT | GGA | GGG | TGG | 1172 |

| | | | | | | | | | | | | | | | | |
|---|---|---|---|---|---|---|---|---|---|---|---|---|---|---|---|---|
| Asp | Cys | Leu | Ser | Ser | Pro | Glu | Gln | Ala | Glu | Pro | Pro | Gly | Gly | Gly | Trp | |
| 340 | | | | 345 | | | | | 350 | | | | | 355 | | |

| CGG | GGA | AGC | CTC | GGG | GAG | CCA | CCA | CCG | CCT | CCA | CGG | GCC | TCA | CTG | AGC | 1220 |
|---|---|---|---|---|---|---|---|---|---|---|---|---|---|---|---|---|
| Arg | Gly | Ser | Leu | Gly | Glu | Pro | Pro | Pro | Pro | Pro | Arg | Ala | Ser | Leu | Ser | |
| | | | | 360 | | | | | 365 | | | | | 370 | | |

| TCG | GAC | ACC | AGC | GCA | CTG | TCC | TAC | GAC | TCT | GTC | AAG | TAC | ACA | CTG | GTG | 1268 |
|---|---|---|---|---|---|---|---|---|---|---|---|---|---|---|---|---|
| Ser | Asp | Thr | Ser | Ala | Leu | Ser | Tyr | Asp | Ser | Val | Lys | Tyr | Thr | Leu | Val | |
| | | | 375 | | | | | 380 | | | | | 385 | | | |

| GTG | GAT | GAG | CAT | GCC | CAG | CTT | GAG | TTG | GTG | AGC | CTG | CGG | CCA | TGT | TTT | 1316 |
|---|---|---|---|---|---|---|---|---|---|---|---|---|---|---|---|---|
| Val | Asp | Glu | His | Ala | Gln | Leu | Glu | Leu | Val | Ser | Leu | Arg | Pro | Cys | Phe | |
| | | 390 | | | | | 395 | | | | | 400 | | | | |

| GGA | GAT | TAC | AGT | GAC | GAA | AGC | GAC | TCT | GCC | ACT | GTC | TAT | GAC | AAC | TGT | 1364 |
|---|---|---|---|---|---|---|---|---|---|---|---|---|---|---|---|---|
| Gly | Asp | Tyr | Ser | Asp | Glu | Ser | Asp | Ser | Ala | Thr | Val | Tyr | Asp | Asn | Cys | |
| 405 | | | | | 410 | | | | | 415 | | | | | | |

| GCC | TCT | GCC | TCC | TCG | CCC | TAC | GAG | TCA | GCC | ATT | GGT | GAG | GAA | TAT | GAG | 1412 |
|---|---|---|---|---|---|---|---|---|---|---|---|---|---|---|---|---|
| Ala | Ser | Ala | Ser | Ser | Pro | Tyr | Glu | Ser | Ala | Ile | Gly | Glu | Glu | Tyr | Glu | |
| 420 | | | | | 425 | | | | | 430 | | | | | 435 | |

| GAG | GCC | CCT | CAA | CCC | CGG | CCT | CCC | ACC | TGC | CTG | TCA | GAG | GAC | TCC | ACA | 1460 |
|---|---|---|---|---|---|---|---|---|---|---|---|---|---|---|---|---|
| Glu | Ala | Pro | Gln | Pro | Arg | Pro | Pro | Thr | Cys | Leu | Ser | Glu | Asp | Ser | Thr | |
| | | | 440 | | | | | 445 | | | | | 450 | | | |

| CCG | GAT | GAG | CCT | GAC | GTC | CAC | TTC | TCT | AAG | AAG | TTT | CTG | AAT | GTC | TTC | 1508 |
|---|---|---|---|---|---|---|---|---|---|---|---|---|---|---|---|---|
| Pro | Asp | Glu | Pro | Asp | Val | His | Phe | Ser | Lys | Lys | Phe | Leu | Asn | Val | Phe | |
| | | 455 | | | | | 460 | | | | | 465 | | | | |

| ATG | AGT | GGC | CGC | TCT | CGT | TCC | TCC | AGT | GCC | GAG | TCC | TTT | GGG | CTG | TTC | 1556 |
|---|---|---|---|---|---|---|---|---|---|---|---|---|---|---|---|---|
| Met | Ser | Gly | Arg | Ser | Arg | Ser | Ser | Ser | Ala | Glu | Ser | Phe | Gly | Leu | Phe | |
| | | 470 | | | | | 475 | | | | | 480 | | | | |

| TCC | TGT | GTC | ATC | AAT | GGG | GAG | GAG | CAT | GAG | CAA | ACC | CAT | CGG | GCT | ATA | 1604 |
|---|---|---|---|---|---|---|---|---|---|---|---|---|---|---|---|---|
| Ser | Cys | Val | Ile | Asn | Gly | Glu | Glu | His | Glu | Gln | Thr | His | Arg | Ala | Ile | |
| | 485 | | | | | 490 | | | | | 495 | | | | | |

| TTC | AGG | TTT | GTG | CCT | CGG | CAT | GAA | GAT | GAA | CTT | GAG | CTG | GAA | GTG | GAC | 1652 |
|---|---|---|---|---|---|---|---|---|---|---|---|---|---|---|---|---|
| Phe | Arg | Phe | Val | Pro | Arg | His | Glu | Asp | Glu | Leu | Glu | Leu | Glu | Val | Asp | |
| 500 | | | | | 505 | | | | | 510 | | | | | 515 | |

| GAC | CCT | CTG | CTG | GTG | GAG | CTG | CAG | GCA | GAA | GAC | TAT | TGG | TAT | GAG | GCC | 1700 |
|---|---|---|---|---|---|---|---|---|---|---|---|---|---|---|---|---|
| Asp | Pro | Leu | Leu | Val | Glu | Leu | Gln | Ala | Glu | Asp | Tyr | Trp | Tyr | Glu | Ala | |
| | | | | 520 | | | | | 525 | | | | | 530 | | |

| TAT | AAC | ATG | CGC | ACT | GGA | GCC | CGT | GGT | GTC | TTT | CCT | GCC | TAC | TAT | GCC | 1748 |
|---|---|---|---|---|---|---|---|---|---|---|---|---|---|---|---|---|
| Tyr | Asn | Met | Arg | Thr | Gly | Ala | Arg | Gly | Val | Phe | Pro | Ala | Tyr | Tyr | Ala | |
| | | | 535 | | | | | 540 | | | | | 545 | | | |

| ATT | GAG | GTC | ACC | AAG | GAG | CCT | GAG | CAC | ATG | GCA | GCC | CTT | GCC | AAA | AAC | 1796 |
|---|---|---|---|---|---|---|---|---|---|---|---|---|---|---|---|---|
| Ile | Glu | Val | Thr | Lys | Glu | Pro | Glu | His | Met | Ala | Ala | Leu | Ala | Lys | Asn | |
| | | 550 | | | | | 555 | | | | | 560 | | | | |

| AGC | GAC | TGG | ATT | GAC | CAG | TTC | CGG | GTG | AAG | TTC | CTG | GGC | TCT | GTC | CAG | 1844 |
|---|---|---|---|---|---|---|---|---|---|---|---|---|---|---|---|---|
| Ser | Asp | Trp | Ile | Asp | Gln | Phe | Arg | Val | Lys | Phe | Leu | Gly | Ser | Val | Gln | |
| | 565 | | | | | 570 | | | | | 575 | | | | | |

| GTT | CCT | TAT | CAC | AAG | GGC | AAT | GAT | GTC | CTC | TGT | GCT | GCT | ATG | CAA | AAG | 1892 |
|---|---|---|---|---|---|---|---|---|---|---|---|---|---|---|---|---|
| Val | Pro | Tyr | His | Lys | Gly | Asn | Asp | Val | Leu | Cys | Ala | Ala | Met | Gln | Lys | |
| 580 | | | | | 585 | | | | | 590 | | | | | 595 | |

| ATC | GCC | ACC | ACC | CGC | CGG | CTC | ACC | GTG | CAC | TTT | AAC | CCG | CCC | TCC | AGC | 1940 |
|---|---|---|---|---|---|---|---|---|---|---|---|---|---|---|---|---|
| Ile | Ala | Thr | Thr | Arg | Arg | Leu | Thr | Val | His | Phe | Asn | Pro | Pro | Ser | Ser | |
| | | | | 600 | | | | | 605 | | | | | 610 | | |

| TGT | GTC | CTT | GAA | ATC | AGC | GTT | AGG | GGT | GTC | AAG | ATA | GGT | GTC | AAA | GCT | 1988 |
|---|---|---|---|---|---|---|---|---|---|---|---|---|---|---|---|---|
| Cys | Val | Leu | Glu | Ile | Ser | Val | Arg | Gly | Val | Lys | Ile | Gly | Val | Lys | Ala | |
| | | | 615 | | | | | 620 | | | | | 625 | | | |

| GAT | GAA | GCT | CAG | GAG | GCC | AAG | GGA | AAT | AAA | TGT | AGC | CAC | TTT | TTC | CAG | 2036 |
|---|---|---|---|---|---|---|---|---|---|---|---|---|---|---|---|---|
| Asp | Glu | Ala | Gln | Glu | Ala | Lys | Gly | Asn | Lys | Cys | Ser | His | Phe | Phe | Gln | |
| | | 630 | | | | | 635 | | | | | 640 | | | | |

| CTA | AAA | AAC | ATC | TCT | TTC | TGT | GGG | TAC | CAT | CCA | AAG | AAC | AAC | AAG | TAC | 2084 |
|---|---|---|---|---|---|---|---|---|---|---|---|---|---|---|---|---|
| Leu | Lys | Asn | Ile | Ser | Phe | Cys | Gly | Tyr | His | Pro | Lys | Asn | Asn | Lys | Tyr | |
| 645 | | | | | 650 | | | | | 655 | | | | | | |

| TTT | GGG | TTT | ATC | ACT | AAG | CAC | CCT | GCT | GAC | CAC | CGG | TTT | GCC | TGC | CAT | 2132 |
|---|---|---|---|---|---|---|---|---|---|---|---|---|---|---|---|---|

|     |     |     |     |     |     |     |     |     |     |     |     |     |     |     |      |
|-----|-----|-----|-----|-----|-----|-----|-----|-----|-----|-----|-----|-----|-----|-----|------|
| Phe | Gly | Phe | Ile | Thr | Lys | His | Pro | Ala | Asp | His | Arg | Phe | Ala | Cys | His  |
| 660 |     |     |     |     | 665 |     |     |     | 670 |     |     |     |     | 675 |      |

```
GTC  TTT  GTG  TCT  GAA  GAT  TCC  ACC  AAA  GCC  CTG  GCA  GAG  TCT  GTG  GGG           2180
Val  Phe  Val  Ser  Glu  Asp  Ser  Thr  Lys  Ala  Leu  Ala  Glu  Ser  Val  Gly
               680                 685                      690

CGT  GCA  TTT  CAG  CAG  TTC  TAC  AAG  CAA  TTT  GTG  GAA  TAT  ACC  TGT  CCT           2228
Arg  Ala  Phe  Gln  Gln  Phe  Tyr  Lys  Gln  Phe  Val  Glu  Tyr  Thr  Cys  Pro
               695                 700                      705

ACA  GAA  GAT  ATC  TAC  TTG  GAG  TAGCAGCAAC  CCCCTCTCT  GCAGCCCTC                      2279
Thr  Glu  Asp  Ile  Tyr  Leu  Glu
               710                 715

AGCCCCAGGC  CAGTACTAGG  ACAGCTGACT  GCTGACAGGA  TGTTGTACTG  CCACGAGAGA                   2339
ATGGGGAGT   GAGGGCTGTT  GGGGTCGGGG  GGCAGGGGTT  TGGGGAGAGG  CAGATGCAGT                   2399
TTATTGTAAT  ATATGGGGTT  AGATTAATCT  ATGGAGGACA  GTACAGGCTC  TCTCGGGGCT                   2459
GGGGAAGGGC  AGGGCTGGGG  TGGGGGTCAG  GCATCTGGCC  ACAAGGGGT   CCCCTAGGGA                   2519
CAGAGGCGCT  GCACCATCCT  GGGCTTGTTT  CATACTAGAG  GCCCTGGCTT  TCTGGCTCTT                   2579
GGGTCCTGCC  TTGACAAAGC  CCAGCCACCT  GGAAGTGTCA  CCTTCCCTTG  TCCACCTCAC                   2639
CCAGTGCCCT  GAGCTCATGC  TGAGCCCAAG  CACCTCCGAA  GGACTTTCCA  GTAAGGAAAT                   2699
GGCAACATGT  GACAGTGAGA  CCCTGTTCTC  ATCTGTGGGG  CTCCGGCAGC  TCCGACCCCC                   2759
AGCCTGGCCA  GCACGCTGAC  CCTGGCAAGC  TTGTGTGTTC  AAAGAAGGAG  AGGGCCACAG                   2819
CAAGCCCTGC  CTGCCAGGGA  AGGTTCCCTC  TCAGCTGGCC  CCAGCCAACT  GGTCACTGTC                   2879
TTGTCACCTG  GCTACTACTA  TTAAAGTGCC  ATTTCTTGTC  TGAAAAAAAA  AAAAAAAAA                    2939
AAAAAAAACT  CGAG                                                                         2953
```

( 2 ) INFORMATION FOR SEQ ID NO:2:

( i ) SEQUENCE CHARACTERISTICS:
    ( A ) LENGTH: 714 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met  Ala  Arg  Leu  Ser  Pro  Gly  Met  Ala  Glu  Arg  Glu  Ser  Gly  Leu  Ser
 1                  5                   10                      15

Gly  Gly  Ala  Ala  Ser  Pro  Pro  Ala  Ala  Ser  Pro  Phe  Leu  Gly  Leu  His
               20                  25                      30

Ile  Ala  Ser  Pro  Pro  Asn  Phe  Arg  Leu  Thr  His  Asp  Ile  Ser  Leu  Glu
               35                  40                      45

Glu  Phe  Glu  Asp  Glu  Asp  Leu  Ser  Glu  Ile  Thr  Asp  Glu  Cys  Gly  Ile
      50                   55                      60

Ser  Leu  Gln  Cys  Lys  Asp  Thr  Leu  Ser  Leu  Arg  Pro  Pro  Arg  Ala  Gly
 65                  70                       75                          80

Leu  Leu  Ser  Ala  Gly  Ser  Ser  Gly  Ser  Ala  Gly  Ser  Arg  Leu  Gln  Ala
               85                  90                      95

Glu  Met  Leu  Gln  Met  Asp  Leu  Ile  Asp  Ala  Ala  Ser  Asp  Thr  Pro  Gly
               100                 105                     110

Ala  Glu  Asp  Asp  Glu  Glu  Asp  Asp  Glu  Leu  Ala  Ala  Gln  Arg  Pro
               115                 120                     125

Gly  Val  Gly  Pro  Ser  Lys  Ala  Glu  Ser  Gly  Gln  Glu  Pro  Ala  Ser  Arg
               130                 135                     140

Ser  Gln  Gly  Gln  Gly  Gln  Gly  Pro  Gly  Thr  Gly  Cys  Gly  Asp  Thr  Tyr
 145                 150                     155                         160
```

-continued

```
Arg  Pro  Lys  Arg  Pro  Thr  Thr  Leu  Asn  Leu  Phe  Pro  Gln  Val  Pro  Arg
               165                      170                      175

Ser  Gln  Asp  Thr  Leu  Asn  Asn  Asn  Ser  Leu  Gly  Lys  Lys  His  Ser  Trp
               180                      185                      190

Gln  Asp  Arg  Val  Ser  Arg  Ser  Ser  Ser  Pro  Leu  Lys  Thr  Gly  Glu  Gln
               195                      200                      205

Thr  Pro  Pro  His  Glu  His  Ile  Cys  Leu  Ser  Asp  Glu  Leu  Pro  Pro  Gln
     210                      215                      220

Gly  Ser  Pro  Val  Pro  Thr  Gln  Asp  Arg  Gly  Thr  Ser  Thr  Asp  Ser  Pro
225                           230                      235                      240

Cys  Arg  Arg  Thr  Ala  Ala  Thr  Gln  Met  Ala  Pro  Pro  Ser  Gly  Pro  Pro
               245                      250                      255

Ala  Thr  Ala  Pro  Gly  Gly  Arg  Gly  His  Ser  His  Arg  Asp  Arg  Ser  Ile
               260                      265                      270

Ser  Ala  Asp  Val  Arg  Leu  Glu  Ala  Thr  Glu  Glu  Ile  Tyr  Leu  Thr  Pro
               275                      280                      285

Val  Gln  Arg  Pro  Pro  Asp  Pro  Ala  Glu  Pro  Thr  Ser  Thr  Phe  Leu  Pro
     290                      295                      300

Pro  Thr  Glu  Ser  Arg  Met  Ser  Val  Ser  Ser  Asp  Pro  Asp  Pro  Ala  Ala
305                           310                      315                      320

Tyr  Ser  Val  Thr  Ala  Gly  Arg  Pro  His  Pro  Ser  Ile  Ser  Glu  Glu  Asp
               325                      330                      335

Glu  Gly  Phe  Asp  Cys  Leu  Ser  Ser  Pro  Glu  Gln  Ala  Glu  Pro  Pro  Gly
               340                      345                      350

Gly  Gly  Trp  Arg  Gly  Ser  Leu  Gly  Glu  Pro  Pro  Pro  Pro  Pro  Arg  Ala
               355                      360                      365

Ser  Leu  Ser  Ser  Asp  Thr  Ser  Ala  Leu  Ser  Tyr  Asp  Ser  Val  Lys  Tyr
     370                      375                      380

Thr  Leu  Val  Val  Asp  Glu  His  Ala  Gln  Leu  Glu  Leu  Val  Ser  Leu  Arg
385                           390                      395                      400

Pro  Cys  Phe  Gly  Asp  Tyr  Ser  Asp  Glu  Ser  Asp  Ser  Ala  Thr  Val  Tyr
               405                      410                      415

Asp  Asn  Cys  Ala  Ser  Ala  Ser  Ser  Pro  Tyr  Glu  Ser  Ala  Ile  Gly  Glu
               420                      425                      430

Glu  Tyr  Glu  Glu  Ala  Pro  Gln  Pro  Arg  Pro  Pro  Thr  Cys  Leu  Ser  Glu
               435                      440                      445

Asp  Ser  Thr  Pro  Asp  Glu  Pro  Asp  Val  His  Phe  Ser  Lys  Lys  Phe  Leu
     450                      455                      460

Asn  Val  Phe  Met  Ser  Gly  Arg  Ser  Arg  Ser  Ser  Ala  Glu  Ser  Phe
465                           470                      475                      480

Gly  Leu  Phe  Ser  Cys  Val  Ile  Asn  Gly  Glu  Glu  His  Glu  Gln  Thr  His
               485                      490                      495

Arg  Ala  Ile  Phe  Arg  Phe  Val  Pro  Arg  His  Glu  Asp  Glu  Leu  Glu  Leu
               500                      505                      510

Glu  Val  Asp  Asp  Pro  Leu  Leu  Val  Glu  Leu  Gln  Ala  Glu  Asp  Tyr  Trp
               515                      520                      525

Tyr  Glu  Ala  Tyr  Asn  Met  Arg  Thr  Gly  Ala  Arg  Gly  Val  Phe  Pro  Ala
     530                      535                      540

Tyr  Tyr  Ala  Ile  Glu  Val  Thr  Lys  Glu  Pro  Glu  His  Met  Ala  Ala  Leu
545                           550                      555                      560

Ala  Lys  Asn  Ser  Asp  Trp  Ile  Asp  Gln  Phe  Arg  Val  Lys  Phe  Leu  Gly
               565                      570                      575

Ser  Val  Gln  Val  Pro  Tyr  His  Lys  Gly  Asn  Asp  Val  Leu  Cys  Ala  Ala
```

```
                       580                        585                         590
Met  Gln  Lys  Ile  Ala  Thr  Thr  Arg  Arg  Leu  Thr  Val  His  Phe  Asn  Pro
          595                      600                     605
Pro  Ser  Ser  Cys  Val  Leu  Glu  Ile  Ser  Val  Arg  Gly  Val  Lys  Ile  Gly
          610                      615                     620
Val  Lys  Ala  Asp  Glu  Ala  Gln  Glu  Ala  Lys  Gly  Asn  Lys  Cys  Ser  His
625                           630                     635                     640
Phe  Phe  Gln  Leu  Lys  Asn  Ile  Ser  Phe  Cys  Gly  Tyr  His  Pro  Lys  Asn
                    645                      650                          655
Asn  Lys  Tyr  Phe  Gly  Phe  Ile  Thr  Lys  His  Pro  Ala  Asp  His  Arg  Phe
               660                      665                     670
Ala  Cys  His  Val  Phe  Val  Ser  Glu  Asp  Ser  Thr  Lys  Ala  Leu  Ala  Glu
          675                      680                     685
Ser  Val  Gly  Arg  Ala  Phe  Gln  Gln  Phe  Tyr  Lys  Gln  Phe  Val  Glu  Tyr
     690                      695                     700
Thr  Cys  Pro  Thr  Glu  Asp  Ile  Tyr  Leu  Glu
705                           710
```

( 2 ) INFORMATION FOR SEQ ID NO:3:

( i ) SEQUENCE CHARACTERISTICS:
        ( A ) LENGTH: 1015 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AACCCTCACT  AAAGGGAACA  AAACGCTGGA  GCTCGCVCGC  CTGCAGGTCG  ACACTACGTG      60
GATCCAAAGA  ATTCCGGCAC  GAGTGCCTGC  CTCTCCGAGG  ACTCCACGCC  TGATGAACCC     120
GACGTCCATT  TCTCCAAGAA  ATTCCTGAAC  GTCTTCATGA  GTGGCCGCTC  CCGCTCCTCC     180
AGTGCTGAGT  CCTTCGGGCT  GTTCTCCTGC  ATCATCAACG  GGGAGGAGCA  GGAGCAGACC     240
CACCGGGCCA  TATTCAGGTT  TGTGCCTCGA  CACGAAGACG  AACTTSAGCT  GGAAGTGGAT     300
GACCCTCTGC  TAGTGGAGCT  CCAGGCTGAA  GACTACTGGT  ACGAGGCCTA  CAACATGCGC     360
ACTGGTGCCC  GGGGTGTCTT  TCCTGCCTAT  TACGCCATCG  AGGTCACCAA  GGAGCCCGAG     420
CACATGGCAG  CCCTGGCCAA  AAACAGTGAC  TGGGTGGACC  AGTTCCGGGT  GAAGTTCCTG     480
GGCTCAGTCC  AGGTTCCCTA  TCACAAGGGC  AATGACGTCC  TCTGTGCTGC  TATGCAAAAG     540
ATTGCCACCA  CCCGCCGGCT  CACCGTGCAC  TTTAACCCGC  CCTCCAGCNG  TGTCCTGGAG     600
ATCAGCGTGC  GGGGTGTGAA  GATAGGCGTC  AAGGCCGATG  ACTCCCAGGA  GGCCAAGGGG     660
AATAAATGTA  GCCACTTTTT  CCAGTTAAAA  AACATCTCTT  TCTGCGGATA  TCATCCAAAG     720
AACAACAAGT  ACTTTGGGTT  CATCACCAAG  CACCCCGCCG  ACCACCGGTT  TGCCTGCCAC     780
GTCTTTGTGT  CTGAAGACTC  CACCAAAGCC  CTGGCAGAGT  CCGTGGGGAG  AGCATTCCAG     840
CAGTTCTACA  AGCAGTTTGT  GGAGTACACC  TGCCCCACAG  AAGATATCTA  CCTGGAGTAG     900
CTGTGCAGCC  CGCCTCTGCG  TCCCCAGCCT  CAGGCCAGTG  CCAGGACAGC  TGGCTGCTGA     960
CAGGATGTGG  CACTGCTTTA  GGAGGGGACT  GCCACCGCCA  GGAGGACAAG  GAAGT         1015
```

( 2 ) INFORMATION FOR SEQ ID NO:4:

( i ) SEQUENCE CHARACTERISTICS:
        ( A ) LENGTH: 270 amino acids
        ( B ) TYPE: amino acid
        ( D ) TOPOLOGY: linear ( x i ) SEQUENCE DESCRIPTION: SEQ ID NO:4:

```
Cys  Leu  Ser  Glu  Asp  Ser  Thr  Pro  Asp  Glu  Pro  Asp  Val  His  Phe  Ser
 1              5                   10                            15

Lys  Lys  Phe  Leu  Asn  Val  Phe  Met  Ser  Gly  Arg  Ser  Arg  Ser  Ser  Ser
               20                   25                       30

Ala  Glu  Ser  Phe  Gly  Leu  Phe  Ser  Cys  Ile  Ile  Asn  Gly  Glu  Glu  Gln
          35                        40                   45

Glu  Gln  Thr  His  Arg  Ala  Ile  Phe  Arg  Phe  Val  Pro  Arg  His  Glu  Asp
     50                        55                       60

Glu  Leu  Xaa  Leu  Glu  Val  Asp  Asp  Pro  Leu  Leu  Val  Glu  Leu  Gln  Ala
 65                      70                        75                        80

Glu  Asp  Tyr  Trp  Tyr  Glu  Ala  Tyr  Asn  Met  Arg  Thr  Gly  Ala  Arg  Gly
               85                        90                             95

Val  Phe  Pro  Ala  Tyr  Tyr  Ala  Ile  Glu  Val  Thr  Lys  Glu  Pro  Glu  His
              100                       105                      110

Met  Ala  Ala  Leu  Ala  Lys  Asn  Ser  Asp  Trp  Val  Asp  Gln  Phe  Arg  Val
          115                       120                      125

Lys  Phe  Leu  Gly  Ser  Val  Gln  Val  Pro  Tyr  His  Lys  Gly  Asn  Asp  Val
     130                      135                      140

Leu  Cys  Ala  Ala  Met  Gln  Lys  Ile  Ala  Thr  Thr  Arg  Arg  Leu  Thr  Val
145                      150                      155                      160

His  Phe  Asn  Pro  Pro  Ser  Ser  Xaa  Val  Leu  Glu  Ile  Ser  Val  Arg  Gly
               165                       170                           175

Val  Lys  Ile  Gly  Val  Lys  Ala  Asp  Asp  Ser  Gln  Glu  Ala  Lys  Gly  Asn
               180                       185                      190

Lys  Cys  Ser  His  Phe  Phe  Gln  Leu  Lys  Asn  Ile  Ser  Phe  Cys  Gly  Tyr
          195                       200                      205

His  Pro  Lys  Asn  Asn  Lys  Tyr  Phe  Gly  Phe  Ile  Thr  Lys  His  Pro  Ala
     210                       215                      220

Asp  His  Arg  Phe  Ala  Cys  His  Val  Phe  Val  Ser  Glu  Asp  Ser  Thr  Lys
225                       230                      235                      240

Ala  Leu  Ala  Glu  Ser  Val  Gly  Arg  Ala  Phe  Gln  Gln  Phe  Tyr  Lys  Gln
               245                       250                      255

Phe  Val  Glu  Tyr  Thr  Cys  Pro  Thr  Glu  Asp  Ile  Tyr  Leu  Glu
               260                       265                      270
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( D ) TOPOLOGY: linear ( x i ) SEQUENCE DESCRIPTION: SEQ ID NO:5:

```
Leu  Cys  Ser  Pro  Pro  Leu  Arg  Pro  Gln  Pro  Gln  Ala  Ser  Ala  Arg  Thr
 1              5                   10                            15

Ala  Gly  Cys
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:6:

```
Gln  Asp  Val  Ala  Leu  Leu
 1              5
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:7:

```
Glu  Gly  Thr  Ala  Thr  Ala  Arg  Arg  Thr  Arg  Lys
 1                  5                        10
```

( 2 ) INFORMATION FOR SEQ ID NO:8:

( i ) SEQUENCE CHARACTERISTICS:
        ( A ) LENGTH: 314 amino acids
        ( B ) TYPE: amino acid
        ( D ) TOPOLOGY: linear ( x i ) SEQUENCE DESCRIPTION: SEQ ID NO:8:

```
Pro  Cys  Phe  Gly  Asp  Tyr  Ser  Asp  Glu  Ser  Asp  Ser  Ala  Thr  Val  Tyr
 1                  5                       10                       15
Asp  Asn  Cys  Ala  Ser  Ala  Ser  Ser  Pro  Tyr  Glu  Ser  Ala  Ile  Gly  Glu
                20                       25                       30
Glu  Tyr  Glu  Glu  Ala  Pro  Gln  Pro  Arg  Pro  Pro  Thr  Cys  Leu  Ser  Glu
           35                       40                       45
Asp  Ser  Thr  Pro  Asp  Glu  Pro  Asp  Val  His  Phe  Ser  Lys  Lys  Phe  Leu
      50                       55                       60
Asn  Val  Phe  Met  Ser  Gly  Arg  Ser  Arg  Ser  Ser  Ala  Glu  Ser  Phe
 65                       70                       75                       80
Gly  Leu  Phe  Ser  Cys  Val  Ile  Asn  Gly  Glu  His  Glu  Gln  Thr  His
                85                       90                       95
Arg  Ala  Ile  Phe  Arg  Phe  Val  Pro  Arg  His  Glu  Asp  Glu  Leu  Glu  Leu
               100                      105                      110
Glu  Val  Asp  Asp  Pro  Leu  Leu  Val  Glu  Leu  Gln  Ala  Glu  Asp  Tyr  Trp
               115                      120                      125
Tyr  Glu  Ala  Tyr  Asn  Met  Arg  Thr  Gly  Ala  Arg  Gly  Val  Phe  Pro  Ala
     130                      135                      140
Tyr  Tyr  Ala  Ile  Glu  Val  Thr  Lys  Glu  Pro  Glu  His  Met  Ala  Ala  Leu
145                      150                      155                      160
Ala  Lys  Asn  Ser  Asp  Trp  Ile  Asp  Gln  Phe  Arg  Val  Lys  Phe  Leu  Gly
                165                      170                      175
Ser  Val  Gln  Val  Pro  Tyr  His  Lys  Gly  Asn  Asp  Val  Leu  Cys  Ala  Ala
               180                      185                      190
Met  Gln  Lys  Ile  Ala  Thr  Thr  Arg  Arg  Leu  Thr  Val  His  Phe  Asn  Pro
          195                      200                      205
Pro  Ser  Ser  Cys  Val  Leu  Glu  Ile  Ser  Val  Arg  Gly  Val  Lys  Ile  Gly
     210                      215                      220
Val  Lys  Ala  Asp  Glu  Ala  Gln  Glu  Ala  Lys  Gly  Asn  Lys  Cys  Ser  His
225                      230                      235                      240
Phe  Phe  Gln  Leu  Lys  Asn  Ile  Ser  Phe  Cys  Gly  Tyr  His  Pro  Lys  Asn
                245                      250                      255
Asn  Lys  Tyr  Phe  Gly  Phe  Ile  Thr  Lys  His  Pro  Ala  Asp  His  Arg  Phe
                260                      265                      270
Ala  Cys  His  Val  Phe  Val  Ser  Glu  Asp  Ser  Thr  Lys  Ala  Leu  Ala  Glu
          275                      280                      285
Ser  Val  Gly  Arg  Ala  Phe  Gln  Gln  Phe  Tyr  Lys  Gln  Phe  Val  Glu  Tyr
     290                      295                      300
```

```
            Thr  Cys  Pro  Thr  Glu  Asp  Ile  Tyr  Leu  Glu
            305                 310
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( D ) TOPOLOGY: linear ( x i ) SEQUENCE DESCRIPTION: SEQ ID NO:9:

```
Gln  Gln  Pro  Pro  Ser  Leu  Gln  Pro  Leu  Ser  Pro  Arg  Pro  Val  Leu  Gly
1                   5                        10                       15

Gln  Leu  Thr  Ala  Asp  Arg  Met  Leu  Tyr  Cys  His  Glu  Arg  Met  Gly  Glu
               20                       25                       30
```

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( D ) TOPOLOGY: linear ( x i ) SEQUENCE DESCRIPTION: SEQ ID NO:10:

```
Gly  Leu  Leu  Gly  Ser  Gly  Gly  Arg  Gly  Leu  Gly  Arg  Gly  Arg  Cys  Ser
1                   5                        10                       15

Leu  Leu
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:11:

```
Tyr  Met  Gly  Leu  Asp
1                   5
```

( 2 ) INFORMATION FOR SEQ ID NO:12:

( i ) SEQUENCE CHARACTERISTICS:
        ( A ) LENGTH: 27 amino acids
        ( B ) TYPE: amino acid
        ( D ) TOPOLOGY: linear ( x i ) SEQUENCE DESCRIPTION: SEQ ID NO:12:

```
Ser  Met  Glu  Asp  Ser  Thr  Gly  Ser  Leu  Gly  Ala  Gly  Glu  Gly  Gln  Gly
1                   5                        10                       15

Trp  Gly  Gly  Gly  Gln  Ala  Ser  Gly  His  Lys  Gly
               20                       25
```

( 2 ) INFORMATION FOR SEQ ID NO:13:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:13:

```
Arg  Thr  Gly  Ala  Arg  Gly  Val  Phe  Pro  Ala  Tyr  Tyr  Ala  Ile  Glu  Val
1                   5                        10                       15

Thr  Lys  Glu  Pro  Glu  His  Met  Ala  Ala  Leu  Ala  Lys  Asn  Ser
               20                       25                       30
```

(2) INFORMATION FOR SEQ ID NO:14:

(i) SEQUENCE CHARACTERISTICS:
    (A) LENGTH: 17 amino acids
    (B) TYPE: amino acid
    (D) TOPOLOGY: linear (xi) SEQUENCE DESCRIPTION: SEQ ID NO:14:

Lys Gly Asn Asp Val Leu Cys Ala Ala Met Gln Lys Ile Ala Thr Thr
1               5                   10                  15
Arg (2) INFORMATION FOR SEQ ID NO:15:

(i) SEQUENCE CHARACTERISTICS:
    (A) LENGTH: 29 amino acids
    (B) TYPE: amino acid
    (D) TOPOLOGY: linear (xi) SEQUENCE DESCRIPTION: SEQ ID NO:15:

Arg Glu Arg Arg Met Ala Asn Asn Ala Arg Glu Arg Leu Arg Val Arg
1               5                   10                  15
Asp Ile Asn Glu Ala Phe Arg Glu Leu Gly Arg Met Cys
            20                  25

(2) INFORMATION FOR SEQ ID NO:16:

(i) SEQUENCE CHARACTERISTICS:
    (A) LENGTH: 16 amino acids
    (B) TYPE: amino acid
    (D) TOPOLOGY: linear (xi) SEQUENCE DESCRIPTION: SEQ ID NO:16:

Lys Leu Leu Ile Leu Gln Gln Ala Val Gln Val Ile Leu Gly Leu Glu
1               5                   10                  15

(2) INFORMATION FOR SEQ ID NO:17:

(i) SEQUENCE CHARACTERISTICS:
    (A) LENGTH: 29 amino acids
    (B) TYPE: amino acid
    (D) TOPOLOGY: linear (xi) SEQUENCE DESCRIPTION: SEQ ID NO:17:

Ala Asp Arg Arg Lys Ala Ala Thr Met Arg Glu Arg Arg Arg Leu Ser
1               5                   10                  15
Lys Val Asn Glu Ala Phe Glu Thr Leu Lys Arg Cys Thr
            20                  25

(2) INFORMATION FOR SEQ ID NO:18:

(i) SEQUENCE CHARACTERISTICS:
    (A) LENGTH: 16 amino acids
    (B) TYPE: amino acid
    (D) TOPOLOGY: linear (xi) SEQUENCE DESCRIPTION: SEQ ID NO:18:

Lys Val Glu Ile Leu Arg Asn Ala Ile Arg Tyr Ile Glu Gly Leu Gln
1               5                   10                  15

(2) INFORMATION FOR SEQ ID NO:19:

(i) SEQUENCE CHARACTERISTICS:
    (A) LENGTH: 29 amino acids
    (B) TYPE: amino acid
    (D) TOPOLOGY: linear (x i) SEQUENCE DESCRIPTION: SEQ ID NO:19:

Asn Val Lys Arg Arg Thr His Asn Val Leu Glu Arg Gln Arg Arg Asn
1               5                   1 0                 1 5

Glu Leu Lys Arg Ser Phe Phe Ala Leu Arg Asp Gln Ile
            2 0                 2 5

(2) INFORMATION FOR SEQ ID NO:20:

(i) SEQUENCE CHARACTERISTICS:
      (A) LENGTH: 16 amino acids
      (B) TYPE: amino acid
      (D) TOPOLOGY: linear (x i) SEQUENCE DESCRIPTION: SEQ ID NO:20:

Lys Val Val Ile Leu Lys Lys Ala Thr Ala Tyr Ile Leu Ser Val Gln
1               5                   1 0                 1 5

(2) INFORMATION FOR SEQ ID NO:21:

(i) SEQUENCE CHARACTERISTICS:
      (A) LENGTH: 29 amino acids
      (B) TYPE: amino acid
      (D) TOPOLOGY: linear (x i) SEQUENCE DESCRIPTION: SEQ ID NO:21:

Lys Glu Arg Arg Val Ala Asn Asn Ala Arg Glu Arg Leu Arg Val Arg
1               5                   1 0                 1 5

Asp Ile Asn Glu Ala Phe Lys Glu Leu Gly Arg Met Cys
            2 0                 2 5

(2) INFORMATION FOR SEQ ID NO:22:

(i) SEQUENCE CHARACTERISTICS:
      (A) LENGTH: 16 amino acids
      (B) TYPE: amino acid
      (D) TOPOLOGY: linear (x i) SEQUENCE DESCRIPTION: SEQ ID NO:22:

Lys Leu Leu Ile Leu His Gln Ala Val Ser Val Ile Leu Asn Leu Glu
1               5                   1 0                 1 5

(2) INFORMATION FOR SEQ ID NO:23:

(i) SEQUENCE CHARACTERISTICS:
      (A) LENGTH: 29 amino acids
      (B) TYPE: amino acid
      (D) TOPOLOGY: linear (x i) SEQUENCE DESCRIPTION: SEQ ID NO:23:

Arg Glu Arg Arg Met Ala Asn Asn Ala Arg Glu Arg Val Arg Val Arg
1               5                   1 0                 1 5

Asp Ile Asn Glu Ala Phe Arg Glu Leu Gly Arg Met Cys
            2 0                 2 5

(2) INFORMATION FOR SEQ ID NO:24:

(i) SEQUENCE CHARACTERISTICS:
      (A) LENGTH: 16 amino acids
      (B) TYPE: amino acid
      (D) TOPOLOGY: linear (x i) SEQUENCE DESCRIPTION: SEQ ID NO:24:

Lys Leu Leu Ile Leu Gln Gln Ala Val Gln Val Ile Leu Gly Leu Glu
1               5                   1 0                 1 5

( 2 ) INFORMATION FOR SEQ ID NO:25:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:25:

GTAAAGGGTG TATTGATTGG ATTACCATCA ATACTCAGCT TCT      43

( 2 ) INFORMATION FOR SEQ ID NO:26:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:26:

GATCTGGAAA CTGCAGCTTC AGCCCTCTG GCCATCTGCT GATCCG      46